US008436050B2

(12) United States Patent
Modak et al.

(10) Patent No.: US 8,436,050 B2
(45) Date of Patent: May 7, 2013

(54) GENTLE-ACTING SKIN-DISINFECTANTS AND HYDROALCOHOLIC GEL FORMULATIONS

(75) Inventors: Shanta Modak, Riveredge, NJ (US); Trupti A. Gaonkar, New York, NY (US); Lauser Caraos, Hollis, NY (US); Lester Sampath, Nyack, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1469 days.

(21) Appl. No.: 10/785,207

(22) Filed: Feb. 24, 2004

(65) Prior Publication Data

US 2004/0247685 A1 Dec. 9, 2004

Related U.S. Application Data

(63) Continuation-in-part of application No. PCT/US02/33865, filed on Oct. 23, 2002, which is a continuation-in-part of application No. 10/047,631, filed on Oct. 23, 2001, now Pat. No. 6,846,846.

(51) Int. Cl.
*A01N 33/12* (2006.01)
*A61K 31/08* (2006.01)
*A61K 31/047* (2006.01)

(52) U.S. Cl.
USPC ........... 514/642; 514/643; 514/722; 514/738; 514/944

(58) Field of Classification Search .................. 514/642, 514/643, 722, 738, 944
See application file for complete search history.

(56) References Cited

U.S. PATENT DOCUMENTS

| | | | |
|---|---|---|---|
| 3,257,276 A * | 6/1966 | Broh-Kahn et al. ........... 514/159 |
| 3,485,915 A | 12/1969 | Gerstien et al. |
| 3,960,745 A | 6/1976 | Billany et al. |
| 4,243,657 A | 1/1981 | Okumura et al. |
| 4,393,076 A * | 7/1983 | Noda et al. ..................... 424/499 |
| 4,478,853 A * | 10/1984 | Chaussee ....................... 514/772 |
| 4,587,266 A | 5/1986 | Verdicchio |
| 4,604,384 A | 8/1986 | Smith et al. |
| 4,664,909 A * | 5/1987 | Marschner ....................... 424/65 |
| 4,670,185 A | 6/1987 | Fujiwara et al. |
| 4,814,334 A | 3/1989 | Salkin |
| 4,853,978 A | 8/1989 | Stockum |
| 4,868,169 A | 9/1989 | O'Laughlin et al. |
| 4,870,108 A * | 9/1989 | Page ............................. 514/642 |
| 4,889,844 A | 12/1989 | Silvetti, Sr. et al. |
| 4,910,205 A | 3/1990 | Kogan et al. |
| 4,919,837 A | 4/1990 | Gluck |
| 4,956,170 A | 9/1990 | Lee |
| 4,963,591 A | 10/1990 | Fourman et al. |
| 4,966,754 A | 10/1990 | Purohit et al. |
| 5,031,245 A | 7/1991 | Milner |
| 5,059,416 A | 10/1991 | Cherukuri et al. |
| 5,073,372 A * | 12/1991 | Turner et al. ................... 424/401 |
| 5,089,205 A | 2/1992 | Huang et al. |
| 5,110,809 A * | 5/1992 | Wang et al. ..................... 514/171 |
| 5,116,602 A | 5/1992 | Robinson et al. |
| 5,133,090 A | 7/1992 | Modak et al. |
| 5,147,648 A | 9/1992 | Bannert |
| 5,164,107 A | 11/1992 | Khan et al. |
| 5,208,031 A | 5/1993 | Kelly |
| 5,357,636 A | 10/1994 | Dresdner, Jr. et al. |
| 5,403,864 A | 4/1995 | Bruch et al. |
| 5,447,930 A | 9/1995 | Nayak |
| 5,516,510 A | 5/1996 | Beilfuss et al. |
| 5,591,442 A * | 1/1997 | Diehl et al. .................... 424/401 |
| 5,599,549 A * | 2/1997 | Wivell et al. ................... 424/401 |
| 5,612,324 A | 3/1997 | Lin et al. |
| 5,624,675 A | 4/1997 | Kelly |
| 5,624,962 A | 4/1997 | Takeuchi et al. |
| 5,648,389 A | 7/1997 | Gans et al. |
| 5,658,575 A | 8/1997 | Ribier et al. |

(Continued)

FOREIGN PATENT DOCUMENTS

| | | |
|---|---|---|
| DE | 4140474 | 6/1993 |
| DE | 4240674 | 3/1994 |

(Continued)

OTHER PUBLICATIONS

Sensiva SC 50 product description from manufacturer website (www.schuelke-mayr.com), Schülke & Mayr, manufacturer, printed Apr. 4, 2001.
Sensiva SC 50 now also approved in Japan, Norderstedt, Aug. 2000, Archived news report from manufacturer website (www.schuelke-mayr.com), Schtilke & Mayr, manufacturer, printed Apr. 4, 2001.
Parfums, Cosmetiques, Aromes: Japan approves sale of new cosmetics ingredient, Chemical Business Newsbase, Jan. 16, 2001.
Prevacare:Antimicrobial Hand Gel product description, Johnson &Johnson, Advanced Wound Care, 2001.

(Continued)

*Primary Examiner* — Fereydoun G Sajjadi
*Assistant Examiner* — Ali Soroush
(74) *Attorney, Agent, or Firm* — Baker Botts, L.L.P.

(57) ABSTRACT

Antimicrobial compositions having synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments include combinations of octoxyglycerin, a quaternary compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin. Hydroalcoholic gel composition containing alcohol, water, hydrogel, and emollient or emulsifier, wherein the composition has a viscosity of below 2000 centipoises at between 20 and 40° C. This skin-friendly hydroalcoholic gel composition, which can be further combined with silicone polymer, emollient solvent, thickening agent and antimicrobial agent, enhances rapid and long-term antimicrobial efficacy.

15 Claims, No Drawings

U.S. PATENT DOCUMENTS

| | | | |
|---|---|---|---|
| 5,705,532 A | 1/1998 | Modak et al. | |
| 5,708,023 A | 1/1998 | Modak et al. | |
| 5,736,574 A * | 4/1998 | Burnier et al. | 514/563 |
| 5,747,021 A * | 5/1998 | McKenzie et al. | 424/73 |
| 5,750,122 A | 5/1998 | Evans et al. | |
| 5,753,270 A | 5/1998 | Beauchamp et al. | |
| 5,763,412 A | 6/1998 | Khan et al. | |
| 5,776,430 A | 7/1998 | Osbourne et al. | |
| 5,804,203 A * | 9/1998 | Hahn et al. | 424/401 |
| 5,827,529 A * | 10/1998 | Ono et al. | 424/448 |
| 5,830,488 A | 11/1998 | Suzuki et al. | |
| 5,869,071 A * | 2/1999 | Wieselman et al. | 424/401 |
| 5,885,562 A | 3/1999 | Lowry et al. | |
| 5,902,572 A | 5/1999 | Luebbe et al. | |
| 5,906,808 A | 5/1999 | Osborne et al. | |
| 5,951,993 A | 9/1999 | Scholz et al. | |
| 5,965,137 A | 10/1999 | Petrus | |
| 5,965,610 A * | 10/1999 | Modak et al. | 514/494 |
| 5,980,477 A | 11/1999 | Kelly et al. | |
| 5,980,925 A | 11/1999 | Jampani et al. | |
| 5,985,918 A | 11/1999 | Modak et al. | |
| 5,985,931 A | 11/1999 | Modak et al. | |
| 5,989,531 A | 11/1999 | Schamper et al. | |
| 6,022,551 A | 2/2000 | Jampani et al. | |
| 6,037,386 A | 3/2000 | Modak et al. | |
| 6,040,347 A * | 3/2000 | Cupferman et al. | 514/723 |
| 6,045,817 A | 4/2000 | Ananthapadmanabhan | |
| 6,107,261 A | 8/2000 | Taylor et al. | |
| 6,110,908 A | 8/2000 | Guthery | |
| 6,136,771 A | 10/2000 | Taylor et al. | |
| 6,183,766 B1 | 2/2001 | Sine et al. | |
| 6,187,327 B1 | 2/2001 | Stack | |
| 6,204,230 B1 | 3/2001 | Taylor et al. | |
| 6,211,243 B1 | 4/2001 | Johnson | |
| 6,248,343 B1 | 6/2001 | Jampani et al. | |
| 6,287,577 B1 | 9/2001 | Beerse | |
| 6,287,583 B1 | 9/2001 | Warren | |
| 6,294,186 B1 | 9/2001 | Beerse et al. | |
| 6,319,958 B1 | 11/2001 | Johnson et al. | |
| 6,321,750 B1 | 11/2001 | Kelly | |
| 6,323,171 B1 | 11/2001 | Fonsny et al. | |
| 6,344,218 B1 | 2/2002 | Dodd et al. | |
| 6,352,701 B1 | 3/2002 | Scholz et al. | |
| 6,376,522 B1 | 4/2002 | Holzl et al. | |
| 6,387,357 B1 | 5/2002 | Chopra et al. | |
| 6,403,067 B1 | 6/2002 | Schamper et al. | |
| 6,403,071 B1 | 6/2002 | Scavone et al. | |
| 6,414,032 B1 | 7/2002 | Johnson | |
| 6,420,431 B1 | 7/2002 | Johnson | |
| 6,426,062 B1 | 7/2002 | Chopra et al. | |
| 6,485,716 B1 * | 11/2002 | Fei et al. | 424/65 |
| 6,511,657 B2 | 1/2003 | Avendano et al. | |
| 6,582,711 B1 | 6/2003 | Amus et al. | |
| 6,613,312 B2 | 9/2003 | Rizvi et al. | |
| 6,682,749 B1 | 1/2004 | Potechin et al. | |
| 6,723,689 B1 | 4/2004 | Hoang et al. | |
| 6,846,846 B2 | 1/2005 | Modak et al. | |
| 7,122,211 B2 | 10/2006 | Jensen et al. | |
| 7,435,429 B2 | 10/2008 | Modak et al. | |
| 7,563,461 B2 | 7/2009 | Modak et al. | |
| 7,745,425 B2 | 6/2010 | Modak et al. | |
| 7,759,327 B2 | 7/2010 | Modak et al. | |
| 7,871,649 B2 | 1/2011 | Modak et al. | |
| 8,207,148 B2 | 6/2012 | Modak et al. | |
| 2002/0022009 A1 | 2/2002 | De La Poterie et al. | |
| 2002/0022660 A1 | 2/2002 | Jampani et al. | |
| 2002/0098159 A1 | 7/2002 | Wei et al. | |
| 2002/0165130 A1 | 11/2002 | Johnson et al. | |
| 2002/0187168 A1 | 12/2002 | Jensen et al. | |
| 2002/0187268 A1 | 12/2002 | Owens et al. | |
| 2003/0134780 A1 | 7/2003 | Patt | |
| 2003/0152644 A1 | 8/2003 | Modak et al. | |
| 2003/0157138 A1 | 8/2003 | Eini et al. | |
| 2003/0211066 A1 | 11/2003 | Scholz | |
| 2004/0102429 A1 * | 5/2004 | Modak et al. | 514/184 |
| 2004/0126604 A1 | 7/2004 | Wang | |
| 2004/0208908 A1 | 10/2004 | Modak et al. | |
| 2004/0219227 A1 | 11/2004 | Modak et al. | |
| 2004/0253275 A1 | 12/2004 | Eini et al. | |
| 2005/0019431 A1 | 1/2005 | Modak et al. | |
| 2005/0048139 A1 | 3/2005 | Modak et al. | |
| 2005/0238602 A1 | 10/2005 | Modak et al. | |
| 2005/0281762 A1 | 12/2005 | Modak et al. | |
| 2006/0141017 A1 | 6/2006 | Kling et al. | |
| 2010/0249227 A1 | 9/2010 | Modak et al. | |
| 2010/0305211 A1 | 12/2010 | Modak et al. | |
| 2011/0070316 A1 | 3/2011 | Modak et al. | |
| 2011/0117140 A1 | 5/2011 | Modak et al. | |
| 2012/0101155 A1 | 4/2012 | Modak et al. | |

FOREIGN PATENT DOCUMENTS

| | | |
|---|---|---|
| DE | 19523320 | 1/1997 |
| EP | 0041448 | 12/1981 |
| EP | 0231080 | 8/1987 |
| EP | 0304802 | 3/1989 |
| EP | 0308210 | 3/1989 |
| EP | 0313302 | 4/1989 |
| EP | 402078 | 12/1990 |
| EP | 0521455 | 1/1993 |
| EP | 0604848 | 7/1994 |
| EP | 0674896 | 10/1995 |
| EP | 0694310 | 1/1996 |
| EP | 1001012 | 5/2000 |
| FR | 2729050 | 7/1996 |
| JP | 1-151522 | 6/1989 |
| JP | 2003-120210 | 5/1991 |
| JP | H09-510976 | 11/1997 |
| JP | 10328284 | 12/1998 |
| JP | 2002-521416 | 7/2002 |
| JP | 2002-527351 | 8/2002 |
| JP | 2003-515615 | 5/2003 |
| JP | 2003-246726 | 9/2003 |
| RU | 2166309 | 5/2001 |
| SU | 833240 | 5/1981 |
| WO | WO84/00111 | 1/1984 |
| WO | WO 87/04350 | 7/1987 |
| WO | WO 88/00795 | 2/1988 |
| WO | WO 88/03799 | 6/1988 |
| WO | WO 89/05645 | 6/1989 |
| WO | WO 93/07903 | 4/1993 |
| WO | WO 93/18745 | 9/1993 |
| WO | WO 93/18852 | 9/1993 |
| WO | WO94/15461 | 7/1994 |
| WO | WO 94/18939 | 9/1994 |
| WO | WO 95/26134 | 10/1995 |
| WO | WO 98/22081 | 5/1998 |
| WO | WO 98/24426 | 6/1998 |
| WO | WO 98/51275 | 11/1998 |
| WO | WO9903463 | 1/1999 |
| WO | WO99/38505 | 8/1999 |
| WO | WO 99/51192 | 10/1999 |
| WO | WO 99/60852 | 12/1999 |
| WO | WO9963816 | 12/1999 |
| WO | WO 00/37042 | 6/2000 |
| WO | WO 00/47183 | 8/2000 |
| WO | WO 01/041573 | 6/2001 |
| WO | WO0303896 | 1/2003 |
| WO | WO0334994 | 5/2003 |
| WO | WO 03/057713 | 7/2003 |
| WO | WO 03/066001 | 8/2003 |
| WO | WO 03/070231 | 8/2003 |
| WO | WO 03/083028 | 10/2003 |
| WO | WO 2004/014416 | 2/2004 |
| WO | WO 2005/009352 | 2/2005 |
| WO | WO 2006/074359 | 7/2006 |
| WO | WO 2006/099359 | 9/2006 |
| WO | WO 2007/069214 | 6/2007 |
| WO | WO 2007/142629 | 12/2007 |

OTHER PUBLICATIONS

Prevacare: Total Solution Skin Care Spray product description, Johnson & Johnson, Advanced Wound Care, 2001.
3M Avagard Surgical and Healthcare Personnel Hand Antiseptic with Moisturizers news release, 3M Company, Jun. 11, 2001.
3M Avagard Surgical and Healthcare Personnel Hand Antiseptic with Moisturizers product description, 3M Company, 2001.

Woodruff, J. "Mixed feelings," Soap Perfumery & Cosmetics, No. 9, vol. 73, p. 39, Sep. 1, 2000.
A-Z of exhibitors; at Central European Coatings Show, PPCJ. Polymers Paint Colour Journal, No. 4433, vol. 190, p. 42, Oct. 1, 2000.
Happi, Household & Personal Products Industry: New ingredients galore at SCC supplier's day, Chemical Business Newsbase, Aug. 1, 2000.
Manufacturing Chemist: Japan approve Schulke & Mayr's Sensiva SC 50, Chemical Business Newsbase, Jul. 14, 2000.
S &M in Japan—Schulke & Mayr's Sensiva SC 50 deodorant active ingredient received approval for use in the Japanese market, SPC Asia No. 21, p. 35, May 2000.
SPC, Soap Perfumery and Cosmetics: New for deodorants: Sensiva SC 50, Chemical Business Newsbase, Aug. 12, 1999.
Beilfuss, "A multifunctional ingredient for deodorants," SOFW Journal, 1998, vol. 124, p. 360, 362-364, 366.
Robinson, K. "Heat beating technology; deodorant market," Soap Perfumery and Cosmetics, v. 69 No. 7 p. 34, Jul. 1996.
Schwarzkopf: Moving into a new area, European Cosmetic Markets, No. 9, Sep. 1, 1996.
Vichy launches oil-free moisturizer, Chemist & Druggist, p. 792, Jun. 8, 1996.
Schwarzkopf cares, European Cosmetic Markets, No. 5, vol. 13, May 1, 1996.
Fraicheur de Peau Fresh Skin Body Mist, International Product Alert, No. 9, vol. 14, May 5, 1997.
U.S. Appl. No. 10/622,272, filed Jul. 17, 2003.
U.S. Appl. No. 10/786,681, filed Feb. 25, 2004.
U.S. Appl. No. 10/047,631, filed Oct. 23, 2001.
U.S. Appl. No. 10/622,272, Sep. 29, 2009 Response to Office Action.
Bleasel et al., 2002, "Allergic contact dermatitis following exposure to essential oils" Australian Journal of Dermatology 43:211-213.
Bush et al., 1986, "Pig skin as test substrate for evaluating topical antimicrobial activity" J Clin Microbiol 24:343-348.
Cimiotti et al., 2003, "Adverse reactions associated with an alcohol-based hand antiseptic among nurses in a neonatal intensive care unit." Am. J. Infect. Control 31:43-48.
Goodman and Gilman's The Pharmacological Basis of Therapeutics, Gilman et al., editors, Seventh Edition, 1985, Macmillan Publishing Company, New York, pp. 959-960, 1066-1067, 1171.
Lansdown, "Interspecies variations in response to topical application of selected zinc compounds," Food Chem Toxicol. Jan. 1991;29(I):57-64.
U.S. Appl. No. 10/622,272, Dec. 21, 2009 Non-Final Office Action.
U.S. Appl. No. 10/786,681, Aug. 27, 2009 Response to non-Final Office Action.
U.S. Appl. No. 10/786,681, Nov. 24, 2009 Final Office Action.
U.S. Appl. No. 10/047,631, Nov. 14, 2003 Non-Final Office Action.
U.S. Appl. No. 10/047,631, Apr. 16, 2004 Response to Non-Final Office Action.
U.S. Appl. No. 10/047,631, Jul. 12, 2004 Notice of Allowance.
Larsen et al., 2001 "Fragrance contact dermatitis: a worldwide multicenter investigation (Part II)" Contact Dermatitis 44:344-346.
Meyer et al., 1978, "The skin of domestic mammals as a model for the human skin, with special reference to the domestic pig." Curf. Problem Dematol 7:39-52.
Modak et al., "A Topical Zinc Gluconate Gel Composition for the Prevention of latex/Starch Glove Related Allergic Reactions: Pilot Study in Volunteers." In: Programs and Abstracts of the 37th Interscience Conference on Antimicrobial Agents and Chemotherapy, Toronto: 1997; American Society for Microbiology Washington DC. Abstract J-52.
Molnycke Healthcare "Hibiclens Antiseptic/Antimicrobial Skin Cleanser" Nov. 10, 2006.
Nair, 2001, "Final report on the safety assessment of Mentha Piperita (Peppermint) oil, Mentha Piperita (Peppermint) Leaf extract, Mentha Piperita (Peppermint) leaf and Mentha Piperita (Peppermint) water," International Journal of Toxicology 20 (Suppl3):61-73.
Pfzer "Purell Instant Hand Sanitizer, Product Description" Nov. 10, 2006.
Rosenthal, S.L., "Effect of Medicaments on the Motility of the Oral Flora with Special Reference to the Treatment of Vincent's Infection" Journal of Dental Research; 1943; vol. 22, pp. 491-494.
Sugiura, 2000, "Results of patch testing with lavender oils in Japan" Contact Dermatitis 43: 157-160.
Vilaplana et al., 2002, "Contact dermatitis from the essential oil of tangerine in fragrances" Contact Dermatitis 46: 108.
Wohrl S, Hemmer W, Focke M, Gotz M, Jarisch R. "The significance of fragrance mix, balsam of Peru, colophony and propolis as screening tools in the detection of fragrance allergy." British Journal of Dermatology 2001; 145(2):268-273.
U.S. Appl. No. 10/622,272, Apr. 21, 2010 Response to Non-Final Office Action.
U.S. Appl. No. 10/622,272, Jul. 22, 2010 Non-Final Office Action.
U.S. Appl. No. 10/786,681, Feb. 24, 2010 Response to Final Office Action.
U.S. Appl. No. 10/786,681, Mar. 30, 2010 Non-Final Office Action.
U.S. Appl. No. 10/892,034, Feb. 8, 2010 Response to Final Office Action.
U.S. Appl. No. 10/892,034, May 17, 2010 Non-Final Office Action.
U.S. Appl. No. 11/327,677, Feb. 23, 2010 Notice of Allowance.
U.S. Appl. No. 11/327,677, Apr. 16, 2010 Amendment after Notice of Allowance.
U.S. Appl. No. 11/327,677, May 10, 2010 Notice of Allowance.
U.S. Appl. No. 11/327,677, May 13, 2010 Response to Amendment under Rule 312.
U.S. Appl. No. 11/446,347, Feb. 26, 2010 Response to Non-Final Office Action.
U.S. Appl. No. 11/446,347, Mar. 15, 2010 Notice of Allowance.
U.S. Appl. No. 11/446,347, May 18, 2010 Amendment after Notice of Allowance.
U.S. Appl. No. 11/446,347, Jun. 2, 2010 Response to Amendment after Notice of Allowance.
U.S. Appl. No. 10/891,624, Mar. 5, 2010 Non-Final Office Action.
U.S. Appl. No. 10/891,624, Jun. 4, 2010 Response to Non-Final Office Action.
U.S. Appl. No. 08/218,666, filed Mar. 28, 1994 (Abandoned).
U.S. Appl. No. 13/532,345, filed Jun. 25, 2012.
U.S. Appl. No. 08/871,071, Jun. 2, 1999 Issue Fee payment.
U.S. Appl. No. 08/871,071, Apr. 16, 1999 Notice of Allowance.
U.S. Appl. No. 08/871,071, Mar. 19, 1999 Response to Non-Final Office Action.
U.S. Appl. No. 08/871,071, Dec. 16, 1998 Non-Final Office Action.
U.S. Appl. No. 08/871,071, Nov. 9, 1998 Response to Non-Final Office Action.
U.S. Appl. No. 08/871,071, May 8, 1998 Non-Final Office Action.
U.S. Appl. No. 09/387,550, Jan. 18, 2000 Issue Fee payment.
U.S. Appl. No. 09/387,550, Nov. 9, 1999 Notice of Allowance.
U.S. Appl. No. 08/218,666, Jun. 24, 1996 Notice of Abandonment.
U.S. Appl. No. 08/218,666, Dec. 18, 1995 Final Office Action.
U.S. Appl. No. 08/821,666, Sep. 7, 1995 Response to Non-Final Office Action.
U.S. Appl. No. 08/821,666, Mar. 3, 1995 Non-Final Office Action.
U.S. Appl. No. 08/821,666, Nov. 18, 1994 Response to Restriction Requirement.
U.S. Appl. No. 08/821,666, Oct. 17, 1994 Restriction Requirement.
U.S. Appl. No. 08/760,054, Sep. 7, 1999 Issue Fee payment.
U.S. Appl. No. 08/760,054, Jun. 21, 1999 Notice of Allowance.
U.S. Appl. No. 08/760,054, Mar. 17, 1999 Response to Non-Final Office Action.
U.S. Appl. No. 08/760,054, Nov. 24, 1998 Non-Final Office Action.
U.S. Appl. No. 08/760,054, Aug. 17, 1998 Continuing Prosecution Application (CPA).
U.S. Appl. No. 08/760,054, May 15, 1998 Advisory Action.
U.S. Appl. No. 08/760,054, Apr. 17, 1998 Notice of Appeal.
U.S. Appl. No. 08/760,054, Nov. 19, 1997 Final Office Action.
U.S. Appl. No. 08/760,054, Jul. 28, 1997 Response to Non-Final Office Action.
U.S. Appl. No. 08/760,054, Mar. 28, 1997 Non-Final Office Action.
U.S. Appl. No. 08/492,080, Sep. 29, 1997 Issue Fee payment.
U.S. Appl. No. 08/492,080, Aug. 6, 1997 Notice of Allowance.
U.S. Appl. No. 08/492,080, Aug. 5, 1997 Examiner Interview Summary.
U.S. Appl. No. 08/492,080, Jul. 9, 1997 Response to Final Office Action.
U.S. Appl. No. 08/492,080, Apr. 9, 1997 Final Office Action.

U.S. Appl. No. 08/492,080, Jan. 13, 1997 Response to Non-Final Office Action.
U.S. Appl. No. 08/492,080, Sep. 13, 1996 Non-Final Office Action.
U.S. Appl. No. 08/492,080, Jun. 28, 1995 Preliminary Amendment.
U.S. Appl. No. 10/891,624, Nov. 30, 2010 Issue Fee payment.
U.S. Appl. No. 10/891,624, Aug. 30, 2010 Notice of Allowance.
U.S. Appl. No. 10/891,624, Jul. 22, 2010 Supplemental Response to Non-Final Office Action.
U.S. Appl. No. 10/892,034, Dec. 17, 2010 Issue Fee payment.
U.S. Appl. No. 10/892,034, Sep. 24, 2010 Notice of Allowance.
U.S. Appl. No. 10/892,034, Aug. 17, 2010 Response to Non-Final Office Action.
U.S. Appl. No. 10/622,272, Apr. 19, 2011 Issue Fee payment.
U.S. Appl. No. 10/622,272, Jan. 19, 2011 Notice of Allowance.
U.S. Appl. No. 10/622,272, Oct. 21, 2010 Response to Non-Final Office Action.
U.S. Appl. No. 11/031,258, Mar. 5, 2008 Issue Fee payment.
U.S. Appl. No. 11/031,258, Dec. 6, 2007 Notice of Allowance.
U.S. Appl. No. 11/031,258, Aug. 22, 2007 Response to Non-Final Office Action and Terminal Disclaimer Filed.
U.S. Appl. No. 11/031,258, Jun. 6, 2007 Non-Final Office Action.
U.S. Appl. No. 11/143,012, Jun. 22, 2009 Issue Fee payment.
U.S. Appl. No. 11/143,012, Mar. 24, 2009 Notice of Allowance.
U.S. Appl. No. 11/143,012, Jan. 16, 2009 Response to Non-Final Office Action and Terminal Disclaimer Filed.
U.S. Appl. No. 11/143,012, Oct. 31, 2008 Non-Final Office Action.
U.S. Appl. No. 11/143,012, Oct. 31, 2007 Preliminary Amendment.
U.S. Appl. No. 12/715,026, May 23, 2012 Issue Fee payment.
U.S. Appl. No. 12/715,026, Feb. 23, 2012 Notice of Allowance.
U.S. Appl. No. 12/715,026, Feb. 6, 2012 Request for Continued Examination (RCE).
U.S. Appl. No. 12/715,026, Feb. 6, 2012 Amendment and Request for Continued Examination (RCE).
U.S. Appl. No. 12/715,026, Nov. 4, 2011 Notice of Allowance.
U.S. Appl. No. 12/715,026, Oct. 27, 2011 Amendment and Request for Continued.
De Groot A, 1997, "Frosch PJ Adverse reactions to fragrances: a clinical review", Contact Dermatitis;36:57-86.
Modak et al., 2005, "A topical cream containing a zinc gel (allergy guard) as a prophylactic against latex glove-related contact dermatitis.", Dermatitis, 16(1):22-7.
de Abreu Gonzaga et al., 2003, "Composition and antibacterial activity of the essential oils from Zanthoxylum rhoifolium", Planta Med.; 69(8):773-775.
Bezic et al., 2003, "Composition and antimicrobial activity of Achillea clavennae L. essential oil", Phytother. Res.; 17(9):1037-1040.
Brehm-Stecher et al., 2003, "Sensitization of Staphylococcus aureus and Escherichia coli to antibiotics by the sesquiterpenoids nerolidol, farnesol, bisabolol, and apritone", Antimicrobial Agents and Chemotherapy; 47(10):3357-3360.
Garcia et al., 2003,"Virucidal activity of essential oils from aromatic plants of San Luis, Argentina." Phytother. Res., 17(9):1073-1075.
Goren et al., 2003, "Analysis of essential oil of Coridothymus capitatus (L.) and its antibacterial and antifungal activity." Z. Naturforsch,. 58(9-10):687-690.
U.S. Appl. No. 12/715,026, Jul. 27, 2011 Notice of Allowance.
U.S. Appl. No. 12/715,026, May 16, 2011 Response to Non-Final Office Action.
U.S. Appl. No. 12/715,026, Nov. 16, 2010 Non-Final Office Action.
U.S. Appl. No. 12/853,977, Jun. 22, 2012 Notice of Allowance.
U.S. Appl. No. 12/853,977, Mar. 12, 2012 Response to Non-Final Office Action.
U.S. Appl. No. 12/853,977, Nov. 10, 2011 Non-Final Office Action.
Hajhashemi et al., 2003, "Anti-inflammatory and analgesic properties of the leaf extracts and essential oil of Lavandula angustifolia Mill." Ethnopharmacol., 89(1 ):67-71.

Minami et al., 2003, "The inhibitory effect of essential oils on herpes simplex virus type-1 replication in vitro." Microbial Immunol., 47(a):681-684.
Paranagama et al., 2003, "Fungicidal and anti-aflatoxigenic effects of the essential oil of Cymbopogon citratus (DC.) Stapf. (lemongrass) against Aspergillus flavus Linle isolated from stored rice." Lett. Appl. Microbiol., 37(1):86-90.
Schuhmacher et al., 2003, "Virucidal effect of peppermint oil on the enveloped viruses herpes simplex virus type 1 and type 2 in vitro." Phytomedicine, 10:504-510.
Shin, 2003, "Anti-Aspergillus activities of plant essential oils and their combination effects with ketoconazole or amphotericin B." Arch. Pharm. Res., 26(5):389-393.
Silva et al., 2003, "Analgesic and anti-inflammatory effects of essential oils of Eucalyptus." Ethnopharmacoi., 89(2-3):277-283.
Valero and Salmera, 2003, "Antibacterial activity of 11 essential oils against Bacillus cereus in tyndallized carrot broth." Int. Food Microbiol., 85(1-2): 73-81.
Velluti et al., 2003, "Inhibitory effect of cinnamon, clove, lemongrass, oregano and palmarose essential oils on growth and fumonisin B1 production by Fusarium proliferatum in maize grain." Int. Food Microbiol., 89: 145-154.
"Drug Information for the Health Care Professional," vol. 1A, USP-D1, 1989, Ninth Edition, pp. 792-793, Banta Company, VIR.
Fitzgerald, K.A., Davies, A., and Russel, A.D., "Mechanism of Action of Chlorhexidine Diacitate and Phenoxyethanol Singly and in Combination Against Gram-negative Bacteria", 215 Mibrobio 70:215-229 (1992).
Heard, D.D., and Ashworth, R.W., "The Colloidal Properties of Chlorhexidine and its Interaction with Some Macromolecules", J. Pharm. Pharmac. 20:505-12, 1968.
Lawrence, J.C. et al., "Evaluation of Phenoxeotol-Chlorhexidine Cream as a Prophylactic Antibacterial Agent in Burns," The Lancet, pp. 1037-1040, May 8, 1992.
Modak S. et al., "Rapid Inactivation of Infections Pathogess by Chlorhexidine Coated Gloves," Infection Control and Hospital Epidemiology, 13:463-471, (1992).
Physicians Desk Reference—39th Edition, 1985, p. 1858, "Lotrisone".
Physicians Desk Reference—39th Edition, 1985, pp. 2037-2038, "chlorhexidine".
Physicians Desk Reference—40th Edition, 1986, pp. 1781-1782, "chlorhexidine".
Rubbo et al., "A Review of Sterilization and Disinfection, Year Book Medical Publishers" Chicago, 161-162 (1965).
Schmolka, I.R., "The Synergistic Effects of Nonionic Surfactants Upon Cationic Germicidal Agents," J. Soc. Cosmet. Chem., 24:577-592, 1973.
Lawless, Julia, "The Illustrated Encyclopedia of Essential Oils: The Complete Guide to the Use of Oils in Aromatherapy and Herbalism", Element Books, 1995, USA. pp. 132,162-164,169,223,227 and 228.
Supplementary European Search Report for EP Application No. 06717623, dated Nov. 5, 2010.
Supplementary European Search Report for EP Application No. 06772072, dated Jun. 6, 2011.
Tanaka et al. "Study on the antiseptics-associated changes in physiological conditions of skin surface." Toyama Medical and Pharmaceutical University. p. 58 (1999).
Ebner et al. Am. J. Clin. Dermatol., vol. 3, No. 6, pp. 427-433. Pub. 2002.
U.S. Appl. No. 12/715,026, filed Mar. 1, 2010.

* cited by examiner

GENTLE-ACTING SKIN-DISINFECTANTS AND HYDROALCOHOLIC GEL FORMULATIONS

The present application is a continuation-in-part of International Application No. PCT/US02/33865, filed on Oct. 23, 2002, and published in English as International Publication No WO03/034994, which is a continuation-in-part of, and claims priority to U.S. patent application Ser. No. 10/047,631, filed Oct. 23, 2001 now U.S. Pat. No. 6,846,846, all of which are incorporated herein in their entireties.

INTRODUCTION

The present invention provides for skin-friendly antimicrobial compositions comprising synergistic combinations of octoxyglycerin and a low concentration of an antibiotic, particularly chlorhexidine. In particular embodiments, the compositions further comprise a quaternary ammonium compound that enhances killing of microbes.

The present invention further provides for skin-friendly hydroalcoholic gel formulations having antimicrobial properties and having properties of enhancing the effect of antimicrobial agents in formulation. In particular, these gel compositions comprise a low concentration of hydrogel soluble in water at ambient temperatures in combination with a low concentration of emulsifier soluble in alcohol at ambient temperature or a low concentration of emollient or mixtures thereof, such that the hydroalcoholic gel formulation has a low viscosity, preferably below 2000 centipoises at 20 to 40° C.

BACKGROUND OF THE INVENTION

"Skin disinfectants" are routinely used in professional and non-professional contexts to rapidly kill microbes. A physician has a need to disinfect his or her skin both before and after examining a patient. Prior to the performance of an invasive medical procedure, the skin of the subject must be properly cleaned to avoid post-procedure infections. In non-professional contexts, a commuter, riding public transportation, may wish to disinfect her hands before handling food; a child, playing in a park, may need to clean his hands but not have the convenience of soap and water nearby. Each of these situations require, optimally, a skin disinfectant that is effective, easy to use, and non-irritating so as to permit repeated use.

A number of skin disinfectants have been developed that use alcohol as the primary antimicrobial agent. There are two general problems associated with alcohol-based disinfectants. First, the effective concentration of alcohol, generally regarded to be greater than about 60 percent weight (hereafter, all percentages should be considered weight/volume percentages, unless specified otherwise) of ethanol, or its equivalent, is irritating to the skin, causing dryness and consequent peeling and cracking. Because chapped skin tends to be more susceptible to microbial contamination, repeated use of alcohol disinfectants can exacerbate the very problem they are intended to solve. Second, whereas alcohol can be an effective disinfectant, once it evaporates its antimicrobial activity is lost.

Alcohol-based skin disinfectants which are known in the art, some of which address the two problems mentioned above, include the following.

U.S. Pat. No. 6,107,261 by Taylor et al., issued Aug. 22, 2000, and its continuations-in-part, U.S. Pat. No. 6,204,230 by Taylor et al., issued Mar. 20, 2001 and U.S. Pat. No. 6,136,771 by Taylor et al., issued Oct. 24, 2000, disclose antibacterial compositions which contain an antibacterial agent at a percent saturation of at least 50 percent. The compositions further comprise, as solubility promoters, a surfactant and a hydric solvent, which may be an alcohol.

U.S. Pat. No. 5,776,430 by Osborne et al., issued Jul. 7, 1998, discloses a topical antimicrobial cleaner containing about 0.65-0.85 percent chlorhexidine and about 50-60 percent denatured alcohol, which is scrubbed onto and then rinsed off the skin.

European Patent Application 0604 848 discloses a gel comprising an antimicrobial agent, 40-90 percent by weight of an alcohol, and a polymer and thickening agent.

U.S. Pat. No. 4,956,170 by Lee, issued Sep. 11, 1990 relates to a high alcohol content antimicrobial gel composition which comprises various emollients and a humectant to protect the skin from the drying effects of the alcohol. In alcohol formulations, higher levels of alcohol are needed to provide instant kill against sensitive as well as resistant strains of bacteria.

Certain formulations virtually omit alcohol as a primary antimicrobial agent, such as, for example, the skin sanitizing compositions disclosed in U.S. Pat. No. 6,187,327 by Stack, issued Feb. 13, 2001, which comprises triclosan (2,4,4'-trichloro-2'-hydroxydiphenyl ether; concentration 0.1-0.35 weight percent) in a topical lotion comprised of a surfactant phase and a wax phase, which purportedly provides antimicrobial protection for 3-4 hours after application. The composition prepared according to the claims of U.S. Pat. No. 6,187,327 further comprises chlorhexidine digluconate.

U.S. Pat. No. 5,965,610 by Modak et al., issued Oct. 12, 1999, teaches skin cleaning compositions comprising antimicrobial agents and zinc salts, where zinc salts have a soothing effect on the skin. The claimed subject matter includes formulations comprising a gel formed between zinc gluconate, chlorhexidine gluconate and a solvent, to which various thickening agents, emulsifying agents and/or emollients may be added.

U.S. Pat. No. 5,985,918 by Modak et al., issued Nov. 16, 1999, relates to "Zinc-Based Anti-Irritant Creams".

U.S. Pat. No. 5,705,532 by Modak et al., issued Jan. 6, 1998, relates to "Triple Antimicrobial Compositions" comprising less than or equal to two percent of a chlorhexidine compound, less than or equal to 0.1 percent of a quaternary ammonium compound, and less than or equal to two percent parachlorometaxylenol.

Octoxyglycerin, sold under the trade name Sensiva® SC50 (Schulke & Mayr), is a glycerol alkyl ether known to be gentle to the skin. Octoxyglycerin exhibits antimicrobial activity against a variety of Gram-positive bacteria associated with perspiration odor, such as *Micrococcus luteus, Corynebacterium aquaticum, Corynebacterium flavescens, Corynebacterium callunae*, and *Corynebacterium nephredi*, and is used in various skin deodorant preparations at concentrations between about 0.2 and 3 percent (Sensiva® product literature, Schulke & Mayr).

For example, U.S. Pat. No. 5,885,562 by Lowry et al., issued Mar. 23, 1999, relates to deodorant compositions comprising an antimicrobial agent, namely polyhexamethylene biguanide (at a concentration of between 0.01 and 0.5 percent), together with a polarity modifier such as Sensiva®SC50, at levels of typically 1-15 percent. Compositions disclosed in U.S. Pat. No. 5,885,562 may further comprise a short chain monohydric alcohol such as ethanol at a level of between 20 and 80 percent. Formulations useful as deodorants, however, would differ from those used as skin sanitizers in that skin sanitizers would optimally exhibit rapid broad spectrum activity against bacteria, fungi, and viruses, not merely gram positive odor causing bacteria.

U.S. Pat. No. 5,516,510 by Beilfuss et al., issued May 14, 1996, discloses deodorant compositions which comprise glycerin monoalkyl ethers such as octoxyglycerin (referred to therein as 2-ethyl hexyl glycerin ether, and as being the most preferred among these compounds). The deodorant compositions of U.S. Pat. No. 5,516,510 may be formulated in aqueous and/or alcoholic solutions and may further comprise additional antimicrobial compounds, including triclosan, chlorhexidine salts, alexidine salts, and phenoxyethanol, among others. Specific concentration ranges for triclosan and the biguanides are not provided.

U.S. Pat. No. 5,951,993 by Scholz et al., issued on Sep. 14, 1999, and U.S. Pat. No. 6,352,701 by Scholz et al., issued Mar. 5, 2002, which is a continuation application thereof, each relate to hydroalcoholic compositions having a lower alcohol and water in a weight ratio of about 35:65 to 100:0, between at least 0.5% and 8.0% by weight thickener system of at least two emulsifiers, wherein each emulsifier is present in at least 0.05% by weight, wherein the composition free of auxiliary thickeners has a viscosity of at least 4000 centipoise at 23° C., and wherein each emulsifier is comprised of at least one hydrophilic group.

U.S. Pat. No. 6,022,551 by Jampani et al., issued Feb. 8, 2000, relates to an antimicrobial alcohol-containing composition containing specified antimicrobial compositions in solution with greater than 30% by volume of alcohol and a carbomer polymer thickener having a viscosity of greater than 9000 centipoise. Optional ingredients further include essential oils, tack modifiers, fragrances, emollients, pH adjusters, viscosity modifiers, transdermal enhancers, sarfactants, dyes, colors and water.

U.S. Pat. No. 5,403,864 by Bruch et al., issued Apr. 4, 1995, relates to alcohol-based solution containing 40-70% by weight of an alcohol or alcohol mixture, antimicrobial compounds such as triclosan and chloroxylenol (PCMX), and optionally includes emollients, surfactants, perfuming agents and chelating agents.

U.S. Pat. No. 4,478,853 by Chausse, issued Oct. 23, 1984, relates to a skin conditioner containing a hydroalcohol gel having from about 35 to 50 percent by weight of a lower alkanol, from about 0.1 to 1 percent by weight of a neutralize gelling agent, wherein the gelling agent is a polyacrylic acid cross-linked with a polyether of an oligosaccharide, and from about 1 to 15 percent by weight of a base composition made of a panthenol moisturizer and an emollient such as a polyhydric alcohol humectant and polyether derivative. The viscosity of these compositions are disclosed to range generally from 2,000 to 20,000 cps.

U.S. Pat. No. 3,485,915 by Gerstein et al., issued Dec. 23, 1969, relates to aqueous and/or alcoholic compositions suitable for topical application to the skin containing, as thickening agents, about 0.1 to about 5 percent by weight of a neutralized carboxy polymer and about 0.1 to about 2 percent by weight of hydroxypropyl cellulose.

A product called Avagard, made by 3M, is commercially available having a combination of emulsifiers, namely Beheneth-10, behenyl alcohol, cetylpalmitate, and diisopropyl dimer dilinoleate with 1% chlorhexidine gluconate solution and 61% ethyl alcohol (w/w).

A product called Prevacare, made by Johnson & Johnson, is commercially available having petrolatum as its active ingredient; water as a vehicle; liposome-building blocks including glycerol distearate, stearate-10, cholesterol, and polysorbate 80; sodium laureth sulfate as a sarfactant; propylene glycol as a moisterizer; and preservatives including diazolidinyl urea, methylparaben, and propylparaben. Prevacare-D is a commercially available product having white petrolatum and dimethicone as active ingredients, and also includes cyclomethicone as an emollient; polyethylene and silica as viscosity builders; mineral oil as a moisturizer/emollient, propylparaben as a preservative and fragrance.

A product called Hibiclens, made by Zeneca Pharmaceuticals, is commercially available having 4 percent chlorhexidine gluconate as its active ingredient. Inactive ingredients include fragrance, isopropyl alcohol, purified water, red #40 and other ingredients not specified in its labelling.

A product called Purell, made by GOJO Industries Inc., is commercially available in four formulations. According to the product literature, the active ingredient in each formulation of Purell is 62 percent ethyl alcohol. Inactive ingredients for Purell 2 in 1 are water, Stearyl Alcohol, Cyclomethicone, C12-15 Alkyl Benzoate, Cetyl Lactate, Cocamidopropyl PG-Dimonium Chloride Phosphate, Glycerin, PEG-4, Propylene Glycol, Tocopheryl Acetate, Aminomethyl Propanol, Carbomer, Styrene/Acrylates Copolymer, Fragrance (Parfum), Diazolidinyl Urea, Iodopropynyl Butylcarbamate, Methylparaben, and Propylparaben; for Purell Original are water, Glycerin, Isopropyl Myristate, Propylene Glycol, Tocopheryl Acetate, Aminomethyl Propanol, Carbomer, and Fragrance (Parfum); for Purell with Aloe are: water, Aloe Barbadensis Leaf Juice, Glycerin, Isopropyl Myristate, Propylene Glycol, Tocopheryl Acetate, Aminomethyl Propanol, Carbomer, Fragrance (Parfum), Blue 1 (CI-42090), Yellow 5 (CI 19140); and for Purell Kid's Own are water, Isopropyl Myristate, Propylene Glycol, Aminomethyl Propanol, Carbomer, Fragrance (Parfum), and Red 33.

SUMMARY OF THE INVENTION

The present invention relates to antimicrobial compositions comprising synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments of the invention comprise combinations of octoxyglycerin, a quaternary ammonium compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin.

Another aspect of this invention relates to skin friendly hydroalcoholic gel formulations that may be used with the antimicrobial composition described above, with other antimicrobial agents or without the inclusion of any additional antimicrobial agents. It has been discovered that these skin friendly hydroalcoholic gel formulations alone possess an antimicrobial effect and also enhance the rapid and sustained effectiveness of additional antimicrobial agents that are added to the gel. Without being bound to any particular theory, it is hypothesized that the formulations of known compositions interfere with the antimicrobial action of the antimicrobial agents.

DETAILED DESCRIPTION OF THE INVENTION

The present invention relates to combinations of octoxyglycerin with at least one, and preferably at least two, antimicrobial agents. In preferred embodiments of the invention such compositions comprise octoxyglycerin and a quaternary ammonium compound.

Octoxyglycerin, as used herein, is also known as glycerol 1-(2-ethylhexyl)ether and is sold under the trade name Sensiva® SC 50 ("Sensiva®") by Schulke & Mayr (Rockaway, N.J.). Octoxyglycerin has the following chemical structure:

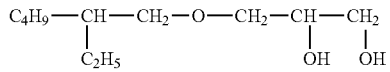

which has the empirical formula $C_{11}H_{24}O_3$. The CAS No. of octoxyglycerin is 70445-33-9. Octoxyglycerin has a relative molecular weight of 204.31 g/mol. Sensiva® SC 50 is sold as a clear, almost colorless liquid, having a refractive index of approximately 1.451, a density at 20° C. of approximately 0.95 g/ml, a boiling point of >285° C., a flash point of 152° C., a water solubility at 22° C. of approximately 1.8 g/l and virtually complete solubility in fat. In addition to having antimicrobial activity, it acts as a mild humectant and skin emollient. The present invention provides for compositions comprising octoxyglycerin at between 1 and 5 percent, and preferably 1-3 percent. It should be noted that all ranges recited herein are inclusive of their limiting values. Sensiva SC50 is essentially pure octoxyglycerin.

Antimicrobial agents which may be used in addition to octoxyglycerin according to the invention include biguanides and phenols. Biguanides may be used in concentrations between about 0.05 and 4 percent and preferably between about 0.05 and 2 percent. Examples of suitable biguanides include polyhexamethylene biguanide (PHMB) at concentrations between about 0.3 and 1 percent, alexidine at concentrations between about 0.05 and 2 percent, and chlorhexidine compounds at concentrations between about 0.05 and 4 percent and preferably between about 0.05 and 1 percent. A chlorhexidine compound, as that term is used herein, includes chlorhexidine free base as well as chlorhexidine salts, including, but not limited to, chlorhexidine diacetate (also known as "chlorhexidine acetate"), chlorhexidine digluconate (also known as "chlorhexidine gluconate"), chlorhexidine palmitate, chlorhexidine diphosphanilate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynaphthoate, and chlorhexidine embonate. Most preferably, the chlorhexidine compound is chlorhexidine digluconate a concentration between 0.05 and 4 percent.

Phenols (phenol derivatives) which may be used according to the invention include, but are not limited to, 2-hydroxyphenol compounds such as triclosan (2,4,4'-trichloro-2'-hydroxydiphenyl ether, also available as IRGASAN DP300 from Ciba Specialty Chemicals Corp, Greensboro, N.C.) and 2,2'-dihydroxy-5,5'-dibromo-diphenyl ether; p-nitrophenol, picric acid, xylenol, phenoxyethanol, chlorinated phenols such as parachlorometaxylenol, p-chloro-o-benzylphenol and -dichlorophenol, cresols such as p-chloro-m-cresol, pyrocatechol, resorcinol, 4-n-hexylresorcinol, pryogallol, phloroglucin, carvacrol, thymol, p-chlorothymol, o-phenylphenol, o-benzylphenol, phenol, 4-ethylphenol, 4-phenolsulfonic acids, hexachlorophene, tetrachlorophene, dichlorophene, 2,3-dihydroxy-5,5'-dichlorophenyl sulfide, 2,2'-dihydroxy-3,3',5,5'-tetrachlorodiphenyl sulfide, 2,2'-dihydroxy-3,3',5,5',6,6'-hexachlorodiphenyl sulfide and 3,3'-dibromo-5,5'-dichloro-2,2'-dihydroxydiphenylamine.

Preferred is triclosan at a concentration of between about 0.1 and 2 percent and most preferably between about 0.3 and 1 percent. Other phenols may be comprised at concentrations of between about 0.3 and 2 percent, but preferably at concentrations equivalent in potency against S. aureus as between 0.3 and 1 percent triclosan.

Additional antimicrobial agents which may be incorporated into compositions of the invention include antifungal agents such as miconazole (preferably at a concentration of 1-2 percent), polymixin (preferably at a concentration of 0.3-1 percent), neomycin (preferably at a concentration of 0.1-0.5 percent), iodine compounds such as povidone iodine (preferably at a concentration of 1-10 percent), minocycline (preferably at a concentration of 0.3-1.0 percent), and metal salts such as silver sulfadiazine (preferably at a concentration of 1-2 percent).

Preferred non-limiting embodiments of the invention comprise octoxyglycerin together with a quaternary ammonium compound, such as, but not limited to, benzalkonium chloride ("BZK", which is particularly preferred), benzethonium chloride, other benzalkonium or benzethonium halides, including, but not limited to, benzalkonium or benzethonium bromide or fluoride, cetyl pyridinium chloride, dequalinium chloride, N-myristyl-N-methyl-morpholinium methyl sulfate, poly[N-[3-(dimethylammonio)propyl]-N'-[3-(ethyleneoxyethelene dimethylammoinio)propyl]urea dichloride], alpha-4-[1-tris(2-hydroxyethyl)ammonium chloride-2-butenyl]-omega-tris(2-hydroxyethyl)ammonium chloride, poly[oxyethylene (dimethyliminio)ethylene (dimethyliminio)-ethylene dichloride]. The concentrations of quaternary ammonium compound may be between about 0.01 and 0.3 percent; preferably the quaternary ammonium compound is benzalkonium chloride at a concentration between 0.05 and 0.2 percent, more preferably between 0.1 and 0.15 percent.

In certain non-limiting embodiments, compositions of the invention may further comprise one or more alcohol. Alcohols which may be used according to the invention include aliphatic alcohols, including, but not limited, most preferred ethanol or isopropyl alcohol, but also n-propyl alcohol, and mixtures thereof, at concentrations between about 20 and 85 percent and preferably 40 to 70 percent. Suitable alcohols also include fatty alcohols, such as cetyl alcohol, myristyl alcohol, stearyl alcohol, octyl alcohol, decyl alcohol, lauryl alcohol, and combinations thereof, at concentrations between about 0.5 and 5 percent. The present invention further provides for compositions comprising, as at least one alcoholic component, hexanol at a concentration of between three and ten percent and preferably about 5 percent.

The formulations of the invention may further comprise one or more of the following:

A zinc-containing compound such as a zinc salt, including but not limited to zinc gluconate, zinc oxide, zinc stearate, zinc salicylate, zinc carbonate, zinc oleate, zinc acetate, zinc peroxide, zinc phosphate, and zinc undecylenate. Zinc compounds are known to have anti-irritant activity (see, for example, U.S. Pat. No. 5,965,610 by Modak et al. and U.S. Pat. No. 5,985,918 by Modak et al., incorporated by reference herein). Preferred zinc compounds for use according to the invention are, for a disinfecting alcohol gel, zinc gluconate and zinc oxide, at concentrations between 0.1 and 1 percent, and preferably 0.8 percent zinc gluconate and 0.2 percent zinc oxide; for an antiseptic aqueous formulation, zinc gluconate and zinc stearate, at concentrations between 0.2 and 7 percent, and preferably 2.4 percent zinc gluconate and 3.8 percent zinc stearate.

An emollient, which may be, for example, an organic, a hydrocarbon-based or a fatty-ester based emollient. Suitable hydrocarbon-based emollients include petrolatum and mineral oils. Suitable fatty ester based emollients include methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

A humectant, such as, for example, glycerine, 1-2-propylene glycol, dipropylene glycol, polyethylene glycol, 1,3-butylene glycol, or 1,2,6-hexanetriol.

A thickening and/or gelling agent, such as, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, behenyl alcohol, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl tri-acetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerine/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl alcohol, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

A neutralizing agent, which may be included, for example, to neutralize carboxyl groups present in one or more other component, such as carboxyl groups in a thickening agent. Suitable neutralizing agents include diisopropylamine and triethanolamine.

A surfactant, which may be an anionic surfactant, a cationic surfactant, an ampholytic surfactant, or a nonionic surfactant, such as, for example, nonionic surfactants such as polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5-2.0%. Suitable concentrations of surfactant are between about 0.05 and 2 percent.

Water used in the formulations is preferably deionized water having a neutral pH.

Additional additives, including but not limited to a silicone fluid (such as dimethicone or cyclomethicone), dyes, fragrances, etc. Examples of additional additives include but are not limited to: pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall Plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

The present invention further relates to hydroalcoholic gel compositions comprising combinations of one percent or less of hydrogel dissolved in water at ambient temperature and three percent or less of emollient dissolved in alcohol or three percent or less of emulsifier wherein said compositions have viocosities below 4000 centipoises at between 20 and 40° C. These percentages and further percentages discussing these hydroalcoholic gel compositions should be considered weight/weight percentages, unless specified otherwise. In preferred embodiments of the invention such compositions comprise 30 to 80 percent alcohol, 15 to 70 percent water, 0.05 to 0.5 percent hydrogel and 0.2 to 3.0 percent emollient and/or 0.05 to 0.5 percent emulsifier with viscosities of less than 2000 cps, most preferably between 50-500 cps. Additional embodiments of this invention further include silicone polymer, emollient solvent, antimicrobial agent, and thickening agent, while maintaining the low viscosities as preferred.

A hydrogel, as used herein, includes hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytomer PC). These hydrogels preferably do not bind to any added antimicrobial agent, therefore leaving the optionally added antimicrobial agent free for rapid and long-term activity. In addition, it has been discovered that alcohol used to form the hydroalcoholic gel is not trapped in the hydroalcoholic gel composition and is therefore available for rapid and long-term action. The hydrogel is present in a concentration between 0.1 and 1.0 percent, and preferably is a cationic hydroxyethyl cellulose (U-care polymers) in a concentration between 0.05 and 0.5 percent, most preferably 0.2 percent.

Alcohols that may be used according to this invention relating to hydroalcoholic gel compositions include the alcohols discussed above, preferably aliphatic alcohols, including, but not limited to, ethenol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol. The concentration of alcohol may be between 30 and 95 percent, preferably between 40 and 70 percent; preferably the aliphitic alcohols is ethanol or isopropyl alcohol at a concentration between and 60 and 95 percent; when present, the concentration of fatty alcohols is preferably between 0.5 and 5.0 percent; and, when present, the concentration of hexanol is preferably between 3 and 10 percent, more preferably 5 percent.

Water, when used in these hydroalcoholic gel compositions, is preferably deionized water having a neutral pH. The present invention provides for compositions comprising water at between 15 and 70 percent. The concentration of water should be suitable to dissolve the hydrogels according to the invention.

An emollient and/or humectant (collectively referred to hereinafter as emollients), as used according to this invention relating to hydroalcoholic gel compositions, include the emollients and humectants discussed above, and preferably include one or more than one PEG 20 Almond Glycerides, Probutyl DB-10, Glucam P20, Glucam E-10, Glucam P-10, Glucam E-20, Glucam P-20 distearate, glycerin, propylene glycol, octoxy glycerin (Sensiva), cetyl acetate and acetylated lanolin alcohol (Acetulan), cetyl ether (PPG-10), myristyl ether (PPG-3), hydroxylated milk glycerides (Cremerol HMG), polyquatemium compounds (U-care compounds), chitosan (Kytamer), copolymer of dimethyl dialyl ammonium chloride and acrylic acid (Merquat), dipropylene glycol methyl ethers (Dowanol DPM, Dow Corning), and polypropylene glycol ethers (Ucon 50-HB-660, Union Carbide). Preferably the emollient is present at a concentration of three percent or less, such that the viscosity of the composition is preferably less than 2000 centipoise at 20 to 40° C., more preferably between 0.2 and 3 percent.

Surfactants and/or emulsifiers (collectively referred to hereinafter as emulsifiers), as used according to this invention relating to hydroalcoholic gel compositions, include the emulsifiers and surfactants discussed above, and preferably include non-ionic or cationic self-emulsifying waxes that are preferably soluble in alcohol at ambient temperature including Incroquat Behenyl TMS, Incroquat Behenyl TMS-50, Polawax, stearyl alcohol and cetearyl alcohol. These emulsifiers are present at a concentration between 0.05 and 3.0 percent. Emulsifiers to this invention preferably include Incroquat Behenyl TMS, which is a mild cationic emulsifier as well as an excellent conditioner, and Polawax, which is a non-ionic self emulsifying wax, individually at a concentration of between 0.05 and 0.5 percent, and incombination at a concentration of between 0.05 and 0.5 percent, more preferably in combination at a concentration ratio of approximately 1:1. If more than one emulsifier is used, it is preferred that the total concentration of all of the emulsifier is between 0.05 and 0.5 percent of the total concentration.

Silicone polymer, as used according to this invention relating to hydroalcoholic gel compositions, includes the silicone polymers discussed above, and preferably includes one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), and silicone glycol (BASF 1066 DCG polyol). Suitable concentrations of silicone polymer are between about 0.1 and 1.0 percent.

Emollient solvents include, but are not limited to, one or more than one glycidyl ethers having alkyl chains up to and including 18 carbon molecules and ethoxylates and propoxylates thereof, glyceryl ethers having alkyl chains up to and including 18 carbon molecules and ethoxylates and propoxylates thereof, mono- and diglyceryl ethers having alkyl chains up to and including 18 carbon molecules and ethoxylates and propoxylates thereof, ethoxylate and propoxylate ethers, ethoxy diglycol esters, ethyl hexyl alcohol propoxylate, and propylene glycol esther ethoxylates and propoxylates, and preferably Arlamol (Altas). Suitable concentrations of emollient solvent are between 0.5 and 5 percent.

Thickening agents that may be used according to this invention relating to hydroalcoholic gel compositions include the thickening agents and gelling agents discussed above, preferably behenyl alcohol, crodamol, and crothix. Suitable concentration of thickening agent are between 0.05 and 1.0 percent. Gelling agents such as Caropol are not preferred due to their high viscosity and their requiring neutralizing agents to neutralize the gelling agent with alkaline materials.

Antimicrobial agents that may be used in addition to the hydroalcoholic gel composition according to the invention include the antimicrobial agents discussed above, including, but not limited to, one or more than one biguanides, phenols, quaternary ammonium compounds and anti-fungal agents. Preferred concentrations are provided above. Preferably, the concentration of the one or more that one antimicrobial agent is less than three percent. More than one antimicrobial agents may be used in combination, such as chlorhexidine gluconate, benzalkonium chloride and phenoxy ethanol, preferably at a concentration of between 0.05 and 0.5 percent, 0.1 and 0.25 percent, and 0.1 and 1.0 percent, respectively. Because cationic antimicrobials, such as biguanides and quaternary ammonium compounds, can bind to the surface of the skin, they may not be available to inactivate pathogens that come into contact with the skin. The gel formulation according to the invention forms a film on the surface of the hand when applied, which film acts as a barrier preventing the antimicrobial agents that may be added to the gel from binding to the surface of the skin.

Ambient temperature is defined herein between 20 and 35° C. Room temperature is defined herein between 20 and 25° C.

Specific, non-limiting embodiments of the invention include the following compositions, which may further comprise additional ingredients that do not substantially effect the antimicrobial properties of the composition. For the following formulations, the water indicated was added last to the other ingredients to bring the total volume to 100 percent. For specific embodiments numbers 11-23, all percentages should be considered weight/weight percentages, unless specified otherwise.

| | | |
|---|---|---|
| 1. | An antiseptic alcohol gel comprising: | |
| | zinc gluconate | 0.8 percent |
| | zinc oxide | 0.2 percent |
| | ethyl alcohol | 65.0 percent (volume/volume) |
| | hydroxy methyl propyl cellulose (K100M) | 0.3 percent |
| | U-care JR 400 (polyquaternium-10) (Amerchol Corp.) | 0.15 percent |
| | Incroquat Behenyl TMS (Croda, Inc.) | 1.0 percent |
| | Polawax A-31 (Croda, Inc.) | 1.0 percent |
| | stearyl alcohol - Crodacol(S70) (Croda, Inc.) | 1.0 percent |
| | Cremerol HMG (Amerchol Corp.) | 1.0 percent |
| | dimethicone | 0.5 percent (volume/volume) |
| | Germall plus (ISP Sutton Laboratories) | 0.25 percent |
| | propylene glycol | 1.5 percent (volume/volume) |
| | glycerin | 1.0 percent (volume/volume) |
| | water | 23.13 percent (volume/volume) |
| | chlorhexidine digluconate | 0.05 percent |
| | phenoxyethanol | 1.0 percent |
| | BZK | 0.12 percent |
| | Sensiva SC50 | 2 percent (volume/volume) |
| | where the gel may be applied to and rubbed over the skin to achieve its antimicrobial effect. | |
| 2. | An antiseptic alcohol gel comprising: | |
| | water | 31.32 percent (volume/volume) |
| | U-care (Amerchol Corp.) | 0.08 percent |
| | hydroxypropylmethylcellulose (K-100) (Dow Corning) | 0.15 percent |
| | Polyox WSR 301 (polyethyleneoxide) (Dow Corning) | 0.03 percent |
| | Incroquat (Croda, Inc.) | 0.4 percent |
| | Polawax A-31(Croda, Inc.) | 0.4 percent |
| | polyethylene glycol | 0.25 percent |
| | ethanol | 63.5 percent (volume/volume) |
| | Glucam E-20 (Amerchol Corp.) | 0.4 percent |
| | Silicone 225 (Dow Corning) | 0.1 percent (volume/volume) |
| | Sensiva SC50 | 2.0 percent (volume/volume) |
| | phenoxyethanol | 1.0 percent |
| | chlorhexidine digluconate | 0.05 percent |
| | BZK | 0.12 percent |
| | Germall Plus (Sutton Laboratories) | 0.2 percent |
| 3. | An antiseptic aqueous formulation comprising: | |
| | zinc gluconate | 2.4 percent |
| | zinc stearate | 3.8 percent |
| | hydroxy methyl propyl cellulose (K100M) | 0.5 percent |
| | Kytamer PC (Chitisan) (Amerchol Corp.) | 0.15 percent |
| | U-care JR 400 (Amerchol Corp.) | 0.1 percent |
| | Incroquat behenyl TMS (Croda, Inc.) | 1.0 percent |
| | Crodamol NM (Croda, Inc.) | 1.6 percent |
| | Acetulan (Amerchol Corp.) | 2.0 percent |
| | Cremerol HMG (Amerchol Corp.) | 1.0 percent |
| | stearyl alcohol | 2.0 percent |
| | allantoin | 0.25 percent |
| | Germall Plus (ISP Sutton Laboratories) | 0.3 percent |
| | dimethicone | 1.0 percent (volume/volume) |
| | water | 81.48 percent (volume/volume) |
| | PHMB | 0.3 percent |
| | phenoxyethanol | 1.0 percent |
| | BZK | 0.12 percent |
| | Sensiva SC50 | 2 percent (volume/volume) |
| 4. | An antimicrobial scrub gel comprising: | |
| | water | 30.5 percent |
| | U-care (Amerchol Corp.) | 0.1 percent |
| | hydroxy propyl methyl cellulose (K100) (Dow Corning) | 0.2 percent |
| | Polyox WSR 301 (polyethyleneoxide) (Dow Corning) | 0.1 percent |
| | Incroquat (Croda, Inc.) | 0.4 percent |
| | Polawax A-31 (Croda, Inc.) | 0.4 percent |
| | propylene glycol | 1.0 percent |
| | ethanol | 63.5 percent (volume/volume) |
| | Glucam E-20 (Amerchol Corp.) | 0.4 percent |
| | Masil SF 19 CG surfactant | 1.0 percent |
| | phenoxyethanol | 1.0 percent |
| | Sensiva SC50 | 1.0 percent (volume/volume) |
| | chlorhexidine digluconate | 0.05 percent |
| | BZK | 0.12 percent |
| | Germall Plus (Sutton Laboratories) | 0.2 percent |
| 5. | An antimicrobial scrub gel, for example for pre-operative skin disinfection, comprising: | |
| | ethanol | 35 percent (volume/volume) |
| | isopropanol | 35 percent (volume/volume) |
| | zinc gluconate | 0.5 percent |
| | zinc oxide | 0.2 percent |
| | hydroxy methyl propyl cellulose (K100M) | 0.3 percent |
| | Germall Plus (ISP Sutton Laboratories) | 0.25 percent |
| | hexanol | 5.0 percent (volume/volume) |
| | PXE | 1.0 percent |
| | Sensiva | 1.5 percent (volume/volume) |
| | chlorhexidine digluconate with water added to 100 percent (approximately 21.2 milliliters/100 ml solution). | 0.05 percent |

6. Another antimicrobial scrub gel, for example for pre-operative skin disinfection, comprising:

| | |
|---|---|
| water | 23.28 percent (volume/volume) |
| Polyox WSR 205 | 0.2 percent |
| U-care JR 400 | 0.2 percent |
| ethanol (95%) | 65 percent (volume/volume) |
| propylene glycol | 3 percent |
| Sensiva SC50 | 2 percent (volume/volume) |
| BZK | 0.12 percent |
| phenoxyethanol | 1.0 percent |
| povidone iodine | 5.0 percent |
| Germall Plus | 0.2 percent |

7. An antimicrobial soap comprising:

| | |
|---|---|
| water | 51.2 percent (volume/volume) |
| U-care (Amerchol Corp.) | 0.1 percent |
| hydroxy propyl methyl cellulose (K-100) (Dow Corning) | 0.2 percent |
| Polyox WSR 301 (polyethyleneoxide) | 0.03 percent |
| ethanol | 40 percent (volume/volume) |
| Pluronic F-87 (BASF) | 2.0 percent |
| Masil SF 19 CG surfactant | 1.0 percent |
| Cocamidopropyl betaine (Witco Corp.) | 2.0 percent |
| propylene glycol | 1.0 percent |
| phenoxyethanol | 1.0 percent |
| chlorhexidine digluconate | 0.05 percent |
| BZK | 0.12 percent |
| Sensiva SC50 | 0.5 percent (volume/volume) |
| Germall Plus (Sutton Laboratories) | 0.2 percent |

8. An antifungal cream comprising miconazole (1-2 percent), chlorhexidine digluconate (0.05-0.2 percent), and Sensiva SC50 (1-3 percent) in a hydrophilic cream base.

9. A topical antiseptic ointment for wound case comprising polymixin (0.3-1%), neomycin (0.1-0.5 percent), chlorhexidine digluconate (0.05-0.2 percent), and Sensiva SC50 (1-3 percent) in a hydrophilic base.

10. A topical antiseptic ointment for burn wound case comprising silver sulfadiazine (1-2 percent), chlorhexidine digluconate (0.05-0.2 percent) and Sensiva SC50 (1-3 percent) in a hydrophilic base.

11. A hydroalcoholic disinfectant gel comprising:

| | |
|---|---|
| Water | 30.6 |
| Polyquaternium-10 (U-careJR30) | 0.2 |
| Kytamer L | 0.1 |
| Ethanol | 65 |
| Incroquat behenyl TMS | 0.8 |
| Polowax A31 | 0.4 |
| Octoxy Glycerin | 2 |
| Chlorhexidine gluconate | 0.05 |
| Benzalkoniumchloride | 0.12 |
| Phenoxyethanol | 0.5 |
| Silicone Glycol (BASF 1066-DCG Polyol) | 0.2 |

12. A hydroalcoholic disinfectant gel comprising:

| | |
|---|---|
| Water | 30.6 |
| Polyquaternium-10 (U-care JR30) | 0.2 |
| Kytamer L | 0.1 |
| Ethanol | 65 |
| Incroquat behenyl TMS | 0.8 |
| Polowax A31 | 0.4 |
| Glycerin | 2 |
| Chlorhexidine gluconate | 0.05 |
| Benzalkoniumchloride | 0.12 |
| Phenoxyethanol | 0.5 |
| Silicone Glycol (BASF 1066-DCG Polyol) | 0.2 |

13. A hydroalcoholic disinfectant gel comprising:

| | |
|---|---|
| Water | 30.6 |
| Hydroxy propyl methyl cellulose (K 100) | 0.2 |
| Kytamer L | 0.1 |
| Ethanol | 65 |
| Incroquat behenyl TMS | 0.8 |
| Polowax A31 | 0.4 |
| Octoxy Glycerin | 2 |
| Chlorhexidine gluconate | 0.05 |
| Benzalkoniumchloride | 0.12 |
| Phenoxyethanol | 0.5 |
| Silicone Glycol (BASF 1066-DCG Polyol) | 0.2 |

14. A hydroalcoholic disinfectant gel comprising:

| | |
|---|---|
| Water | 30.6 |
| Hydroxy propyl methyl cellulose (K 100) | 0.2 |
| Kytamer L | 0.1 |
| Ethanol | 65 |
| Incroquat behenyl TMS | 0.8 |
| Polowax A31 | 0.4 |
| Glycerin | 2 |
| Chlorhexidine gluconate | 0.05 |
| Benzalkoniumchloride | 0.12 |
| Phenoxyethanol | 0.5 |
| Silicone Glycol (BASF 1066-DCG Polyol) | 0.2 |

15. A hydroalcoholic surgical scrub comprising:

| | |
|---|---|
| Water | 26.8 |
| U care JR30 | 0.3 |
| Ethanol | 70 |
| Octoxy Glycerin | 2 |
| Silicone Glycol (BASF 1066-DCG Polyol) | 0.2 |
| Chlorhexidine gluconate | 0.05 |
| Benzalkoniumchloride | 0.12 |
| Phenoxyethanol | 0.5 |

16. A hydroalcoholic surgical scrub comprising:

| | |
|---|---|
| Water | 26.8 |
| U care JR30 | 0.3 |
| Ethanol | 70 |
| Glycerin | 2 |
| Silicone Glycol (BASF 1066-DCG Polyol) | 0.2 |
| Chlorhexidine gluconate | 0.05 |
| Benzalkoniumchloride | 0.12 |
| Phenoxyethanol | 0.5 |

17. A hydroalcoholic antimicrobial scrub, for example for pre-operative skin disinfection, comprising:

| | |
|---|---|
| Water | 26.8 |
| U care JR30 | 0.3 |
| Isopropanol | 70 |
| Octoxy Glycerin | 2 |
| Silicone Glycol (BASF 1066-DCG Polyol) | 0.2 |
| Chlorhexidine gluconate | 0.05 |
| Benzalkoniumchloride | 0.12 |
| Phenoxyethanol | 0.5 |

18. A hydroalcoholic antimicrobial scrub, for example for pre-operative skin disinfection, comprising:

| | |
|---|---|
| Water | 24.8 |
| U care JR30 | 0.3 |
| Ethanol | 62 |
| Octoxy Glycerin | 2 |
| Silicone Glycol (BASF 1066-DCG Polyol) | 0.2 |
| Chlorhexidine gluconate | 0.05 |
| Benzalkoniumchloride | 0.12 |
| Phenoxyethanol | 0.5 |
| Povidone Iodine | 10 |

19. A hydroalcoholic antimicrobial soap comprising:

| | |
|---|---|
| Ethanol | 52 |
| Pluronic F-87 | 2 |
| Masil SF19(Silicone surfactant) | 1 |
| Masil 1066 | 1 |
| Cocamidopropyl betaine | 1 |
| Mirapol A-15 | 1 |
| Water | 35.5 |
| U-care JR30 | 0.1 |
| Polyox WOR-205 | 0.2 |
| Germall Plus | 0.2 |
| CHG | 0.05 |
| BZK | 0.12 |
| Propylene glycol | 2 |
| Glycerin | 2 |
| Octoxy glycerin | 1 |
| Phenoxyethanol | 0.5 |

20. A hydroalcoholic disinfectant gel comprising:

| | |
|---|---|
| Water | 31.73 |
| Polyquaternium-10 (U-careJR30) | 0.2 |
| Ethanol | 65 |
| Incroquat behenyl TMS | 0.4 |
| Octoxy Glycerin | 2 |
| Chlorhexidine gluconate | 0.05 |
| Benzalkoniumchloride | 0.12 |
| Phenoxyethanol | 0.5 |

-continued

21. A hydroalcoholic disinfectant gel comprising:
    Water                               31.73
    Polyquaternium-10 (U-careJR30)       0.2
    Ethanol                             65
    Incroquat behenyl TMS                0.4
    Glycerin                             2
    Chlorhexidine gluconate              0.05
    Benzalkoniumchloride                 0.12
    Phenoxyethanol                       0.5
22. A hydroalcoholic disinfectant gel comprising:
    Water                               33.73
    Polyquaternium-10 (U-careJR30)       0.2
    Ethanol                             65
    Isopropanol                          5
    Incroquat behenyl TMS                0.4
    Octoxy Glycerin                      2
    Chlorhexidine gluconate              0.05
    Benzalkoniumchloride                 0.12
    Phenoxyethanol                       0.5
23. A hydroalcoholic disinfectant gel comprising:
    Water                               26.73
    Polyquaternium-10 (U-careJR30)       0.2
    Ethanol                             65
    Isopropanol                          5
    Incroquat behenyl TMS                0.4
    Glycerin                             2
    Chlorhexidine gluconate              0.05
    Benzalkoniumchloride                 0.12
    Phenoxyethanol                       0.5

EXAMPLES

Example 1

Sensiva+BZK

Sensiva SC50 and/or benzalkonium chloride ("BZK") were added, in various concentrations, to the following alcohol gel base:

| | |
|---|---|
| ethyl alcohol | 65 percent (volume/volume) |
| hydroxy methyl propyl cellulose (K100M) | 0.3 percent |
| hydroxy propyl cellulose (HF) | 0.1 percent (volume/volume) |
| Glucam P20 | 1.0 percent (volume/volume) |
| Glucam P20 distearate | 1.5 percent (volume/volume) |
| U-care JR 400 (polyquaternium-10) | 0.15 percent |
| silicone (DC 1403) | 1.5 percent (volume/volume) |
| Germall Plus | 0.25 percent | to which water was added, after the incorporation of other additives, to bring the total volume to 100 percent (typically requiring approximately 20-30 percent (volume/volume)). The amount of Sensiva, throughout the example section, is a volume/volume percentage.

Antimicrobial activity was evaluated using the following assay. 1 milliliter of $10^8$ colony-forming units ("cfus") of test organism per milliliter was added to 1 milliliter of bovine adult serum in a sterile culture tube and mixed. 1 milliliter of the test gel was added to each tube, and was vortexed to mix. After 15 seconds, three 0.5 ml aliquots were removed and further diluted 1:1000 with LTSB (lecithin-containing trypticase soy broth) drug-inactivating medium, and, of the resulting liquid, 0.5 milliliters were plated on each trypticase soy agar ("TSA") plate. The resulting plates were incubated at 37° C. for 24 hours and the colony count per tube was determined.

The foregoing method was used to determine the antimicrobial activities of formulations of the above alcohol gel base comprising either Sensiva SC50, BZK or combinations of Sensiva SC50 and BZK. The results for Sensiva SC50 used alone are shown in Table 1, and the results for Sensiva SC50, BZK and Sensiva SC50/BZK combinations are shown in Table 2.

TABLE 1

| | % Sensiva | | | | | |
|---|---|---|---|---|---|---|
| | 0 | 0.5 | 1.0 | 2.0 | 3.0 | 5.0 |
| S. aureus (cfu/tube) | $1 \times 10^8$ | $1 \times 10^7$ | $4 \times 10^7$ | $3 \times 10^6$ | $1 \times 10^6$ | $1 \times 10^6$ |
| fold-reduction* | — | 2.5 | 9 | 33 | 100 | 100 |

*relative to control

TABLE 2

| | % Sensiva | | | | | | | | | |
|---|---|---|---|---|---|---|---|---|---|---|
| | 0 | 1.0 | 2.0 | 0 | 0 | 0 | 1.0 | 1.0 | 2.0 | 2.0 |
| % BZK | 0 | 0 | 0 | 0.12 | 0.19 | 0.5 | 0.12 | 0.19 | 0.12 | 0.19 |
| S. aureus (cfu/tube) | $1 \times 10^8$ | $4 \times 10^7$ | $3 \times 10^6$ | $1.6 \times 10^7$ | $2 \times 10^7$ | $3.7 \times 10^6$ | $8 \times 10^5$ | $2 \times 10^4$ | $8 \times 10^3$ | $3.0 \times 10^3$ |
| Log 10 cfu reduction relative to control | — | 1 | 1.5 | 0.8 | 0.7 | 1.4 | 2.1 | 3.7 | 4.1 | 4.5 |
| Increase in log 10 beyond additive effect | NA | NA | NA | NA | NA | NA | 0.3 | 2 | 1.8 | 2.3 |

TABLE 2-continued

| | \% Sensiva | | | | | | | | | |
|---|---|---|---|---|---|---|---|---|---|---|
| | 0 | 1.0 | 2.0 | 0 | 0 | 0 | 1.0 | 1.0 | 2.0 | 2.0 |
| fold reduction relative to control | — | 10 | 33 | 6.25 | 5 | 27 | 125 | $5 \times 10^3$ | $1.25 \times 10^4$ | $3.3 \times 10^4$ |

Tables 1 and 2 show that no significant antimicrobial activity against *S. aureus* was obtained with 2-5 percent Sensiva; the antimicrobial activity was not significantly different between 2, 3 and 5 percent of Sensiva. Similarly, 0.12 and 0.19 percent BZK exhibited minimal or no antimicrobial activity (Table 2). However, combinations of 1-2 percent Sensiva SC50 and 0.12-0.19 percent BZK showed 5000-33000 fold reduction in colony-forming units compared to control values (Table 2).

Example 2

Sensiva+Chlorhexidine Digluconate

Assays using the same gel base and protocol as set forth in Example 1 to test activities of Sensiva, chlorhexidine digluconate ("CHG"), and combinations thereof gave the following results, shown in Table 3.

TABLE 3

| | \% Sensiva | | | | | | | | | |
|---|---|---|---|---|---|---|---|---|---|---|
| | 0 | 0 | 0 | 0 | 1.0 | 1.0 | 1.0 | 2.0 | 2.0 | 2.0 |
| % CHG | 0 | 0.05 | 0.25 | 0.5 | 0.05 | 0.25 | 0.5 | 0.05 | 0.25 | 0.5 |
| S. aureus (cfu/tube) | $1 \times 10^8$ | $1.1 \times 10^7$ | $8 \times 10^6$ | $4.2 \times 10^6$ | $1.2 \times 10^5$ | $6 \times 10^4$ | $8 \times 10^3$ | $8 \times 10^3$ | $5 \times 10^3$ | $1 \times 10^3$ |
| Log 10 cfu reduction relative to control | — | 1.0 | 1.1 | 1.4 | 2.9 | 3.1 | 4.1 | 4.1 | 4.3 | 4.3 |
| Increase in log 10 beyond additive effect | NA | NA | NA | NA | 0.4 | 1.1 | 1.7 | 1.6 | 1.7 | 2.4 |
| fold reduction relative to control | — | 9 | 12.5 | 23.8 | 833 | 1666 | 12500 | 12500 | 20000 | $1 \times 10^5$ |

Thus, Sensiva SC50 (1-2 percent) and CHG (0.05-0.5 percent) used individually showed 9-35 fold reduction in colony counts as compared to control, whereas a combination of 1-2 percent Sensiva with 0.05-0.5 percent CHG showed 800-100,000 fold reduction. Thus, the combination of Sensiva and CHG appears to be synergistic. When benzalkonium chloride was added to formulation, the antimicrobial activity was improved still further, as shown in the following example section.

Example 3

Sensiva+Chlorhexidine Digluconate+BZK

Assays using the same gel base and protocol as set forth in Example 1 to test activities of combinations of Sensiva, chlorhexidine digluconate ("CHG") and BZK gave the following results, shown in Table 4.

TABLE 4

| % Sensiva | 0 | 0 | 1.0 | 2.0 |
|---|---|---|---|---|
| % BZK | 0 | 0.12 | 0.12 | 0.12 |
| % CHG | 0 | 0.05 | 0.05 | 0.05 |
| Growth (cfu/ml) | $1 \times 10^8$ | $1.2 \times 10^7$ | $4 \times 10^4$ | 0 |
| Log 10 cfu reduction relative to control | 0 | 1.0 | 4.0 | 8.0 |
| Increase in log 10 beyond additive effect | NA | NA | 2.1 | 5.1 |
| fold reduction relative to control | — | 8.3 | 2500 | 108 |

NA = not applicable

Example 4

Combinations of Sensiva and Other Antimicrobials

Since Sensiva does not exhibit potent microbicidal activity even at concentrations of between 3 and 5 percent, it is surprising that this compound exhibits synergism with chlorhexidine digluconate and BZK. Octoxyglycerin (Sensiva) has been reported to have the property of deeper penetration into the upper layers of the epidermis. Without being bound by any particular theory, the mechanism of synergistic action may be explained as follows. When a bacterium is exposed to Sensiva and a second antimicrobial agent, Sensiva may penetrate through the bacterial cell wall and thereby compromise the bacterial transport system. This may result in increased uptake of the second antimicrobial agent. This mechanism would indicate that Sensiva would promote the antimicrobial effects of a diverse array of compounds, including quaternary ammonium compounds, biguanides, chlorinated phenols, metal salts, antifungal azoles, etc.

Accordingly, the antimicrobial activity of various combinations of Sensiva and other antimicrobials was tested, using concentrations that fall within the recommended usage range for topical formulations. The following agents were tested. Benzalkonium chloride (BZK) and benzethonium chloride (BZT) were tested as representative of the class of quaternary ammonium compounds. Chlorhexidine digluconate (CHG) and polyhexamethylene biguanide (PHMB) were tested as representative of the class of biguanides. Parachlorometaxylenol (PCMX) and triclosan (TC) were tested as representative of the class of chlorinated phenols. Povidone iodine (PVI) was tested as representative of the class of iodine compounds. Silver sulfadiazine (AgSD) was tested as representative of the class of metal salts. Neomycin and miconazole were tested as representative of the class of antibiotics. The alcohol gel base and protocol set forth in Example 1 were used to produce the data set forth in Table 5.

Similar protocols were then used to test the antibacterial activity of Sensiva combined with chlorhexidine digluconate and another antimicrobial agent. The results are shown in Table 6.

TABLE 5

| % Antimicrobial | % Sensiva | Growth (CFU/ml) | fold reduction* |
|---|---|---|---|
| 0 Control | 0 | $1 \times 10^8$ | — |
| 0 | 2.0 | $3 \times 10^6$ | 33 |
| BZK | | | |
| 0.12 | 0 | $1.6 \times 10^7$ | 6.25 |
| 0.12 | 2.0 | $8.0 \times 10^3$ | 12500 |
| BZT | | | |
| 0.12 | 0 | $1.0 \times 10^7$ | 10 |
| 0.12 | 2.0 | $5.0 \times 10^3$ | 20,000 |
| CHG | | | |
| 0.05 | 0 | $1.1 \times 10^7$ | 9 |
| 0.05 | 2.0 | $8.0 \times 10^3$ | 12,500 |
| PHMB | | | |
| 0.3 | 0 | $3.0 \times 10^6$ | 33 |
| 0.3 | 2.0 | $4.0 \times 10^3$ | 25,000 |
| TC | | | |
| 0.3 | 0 | $1.0 \times 10^8$ | 0 |
| 0.3 | 2.0 | $2.2 \times 10^5$ | 450 |
| PCMX | | | |
| 0.3 | 0 | $1.0 \times 10^8$ | 0 |
| 0.3 | 2.0 | $6.2 \times 10^4$ | 1612 |
| AgSD | | | |
| 1.0 | 0 | $1.0 \times 10^8$ | 0 |
| 1.0 | 2.0 | $3.0 \times 10^5$ | 330 |
| PVI | | | |
| 1.0 | 0 | $2.0 \times 10^7$ | 5 |
| 1.0 | 2.0 | $3.0 \times 10^4$ | 3,333 |
| Neomycin | | | |
| 0.3 | 0 | $2.3 \times 10^7$ | 4.3 |
| 0.3 | 2.0 | $1.0 \times 10^3$ | 100,000 |
| Miconazole | | | |
| 1.0 | 0 | $1.0 \times 10^8$ | 0 |
| 1.0 | 2.0 | $6.0 \times 10^4$ | 1666 |

*relative to control

TABLE 6

| % Antimicrobial | % Sensiva | % CHG | Growth (CFU/ML) | Fold Reduction Compared to Control |
|---|---|---|---|---|
| 0 | 0 | 0 | $1.0 \times 10^8$ | — |
| 0 | 2.0 | 0 | $3.0 \times 10^6$ | 33 |
| 0 | 2.0 | 0.05 | $8.0 \times 10^3$ | 12,500 |
| BZK | | | | |
| 0.12 | 0 | 0.05 | $1.2 \times 10^7$ | 8.3 |
| 0.12 | 2.0 | 0.05 | 0 | $10^8$ |
| TC | | | | |
| 0.3 | 0 | 0.05 | $9.0 \times 10^6$ | 11.1 |
| 0.3 | 2.0 | 0.05 | 0 | $10^8$ |
| PCMX | | | | |
| 0.3 | 0 | 0.05 | $7.0 \times 10^6$ | 14.2 |
| 0.3 | 2.0 | 0.05 | 0 | $10^8$ |
| AgSD | | | | |
| 1.0 | 0 | 0.05 | $1.0 \times 10^7$ | 10 |
| 1.0 | 2.0 | 0.05 | 0 | $10^8$ |
| PVI | | | | |
| 1.0 | 0 | 0.05 | $1.0 \times 10^7$ | 10 |
| 1.0 | 2.0 | 0.05 | 0 | $10^8$ |
| Neomycin | | | | |
| 0.3 | 0 | 0.05 | $1.0 \times 10^6$ | 100 |
| 0.3 | 2.0 | 0.05 | 0 | $10^8$ |

The data shown in Table 5 indicate that Sensiva, at a concentration of 2.0 percent, produced a 33-fold reduction in bacterial colony formation, and the antibacterial activity of the other antimicrobials tested, used alone, was less than or equal to 33-fold. Combination of these antimicrobials with Sensiva greatly resulted in an antibacterial activity greater than what would have been expected, based on the inhibitory activity of either agent used separately. The extent of this enhancement varied among antimicrobials; for example, the activity of quaternary ammonium compounds, used in combination with Sensiva, was observed to be 12,500 and 20,000-fold greater than control. The biguanides chlorhexidine digluconate and parahexamethylenebiguanide, in combination with Sensiva, produced an antimicrobial activity 12,500 and 25.000-fold greater, respectively, than control. Neomycin, in combination with Sensiva, exhibited an antimibrobial activity 100,000 greater than control. Thus, Sensiva has been demonstrated to enhance the antimicrobial effects of a wide variety of agents. The data shown in Table 6 further show that combinations of Sensiva and chlorhexidine digluconate with various antimicrobials exhibit a further enhancement in activity.

Example 5

Additional Data

Assays using the same gel base and protocol as set forth in Example 1 to test activities of combinations of Sensiva and other antimicrobials gave the following results, shown in Table 7.

TABLE 7

| Agent(s) | Concentrations | Growth (cfu/tube) |
| --- | --- | --- |
| control (without gel base) | — | $2.5 - 4.2 \times 10^8$ |
| Sensiva | 0.5 | $4.0 \times 10^7$ |
| Sensiva | 1.0 | $1.0 \times 10^7$ |
| BZK | 0.019 | $8.0 \times 10^7$ |
| BZK + | 0.019 | $2.0 \times 10^7$ |
| Sensiva | 1.0 | |
| BZK+ | 0.019 | $1.2 \times 10^7$ |
| Sensiva | 2.0 | |
| BZK | 0.12 | $1.6 \times 10^7$ |
| BZK+ | 0.12 | $1.4 \times 10^7$ |
| Sensiva | 0.5 | |
| BZK + | 0.12 | $8.0 \times 10^5$ |
| Sensiva | 1.0 | |
| CHG | 0.05 | $1.1 \times 10^7$ |
| CHG + | 0.05 | $6.3 \times 10^6$ |
| Sensiva | 0.5 | |
| CHG + | 0.05 | $1.2 \times 10^5$ |
| Sensiva | 1.0 | |
| PCMX | 0.15 | $3.5 \times 10^8$ |
| PCMX + | 0.15 | $4.1 \times 10^5$ |
| Sensiva | 2.0 | |
| TC + | 0.3 | $1.0 \times 10^7$ |
| BZK | 0.12 | |
| TC + | 0.3 | $4.0 \times 10^3$ |
| BZK + | 0.12 | |
| Sensiva | 2.0 | |
| PCMX + | 0.3 | $2.0 \times 10^6$ |
| BZK | 0.12 | |
| PCMX + | 0.3 | $1.0 \times 10^3$ |
| BZK + | 0.12 | |
| Sensiva | 2.0 | |
| Miconazole + | 1.0 | $1.0 \times 10^7$ |
| CHG | 0.05 | |
| Miconazole + | 1.0 | $1.0 \times 10^3$ |
| CHG + | 0.05 | |
| Sensiva | 2.0 | |
| PVI + | 1.0 | $1.0 \times 10^7$ |
| CHG | 0.05 | |
| PVI + | 1.0 | 0 |
| CHG + | 0.05 | |
| Sensiva | 2.0 | |

Example 6

Combinations of Sensiva, BZK, and Other Agents

Again using the alcohol gel base and protocol described in Example 1, various combinations of Sensiva, the quaternary ammonium compound BZK, and other antimicrobials produced the results shown in Table 8.

TABLE 8

| Agent(s) | Concentration (%) | Growth (cfu/tube) |
| --- | --- | --- |
| Control (no gel base) | — | $2.0 \times 10^8$ |
| Control (gel base) | — | $1.2 \times 10^8$ |
| PXE | 1.0 | $1.0 \times 10^8$ |
| PXE + | 1.0 | $2.0 \times 10^7$ |
| Sensiva | 1.0 | |
| PXE + | 1.0 | $3.3 \times 10^5$ |
| Sensiva | 2.0 | |
| BZK + | 0.12 | $4.0 \times 10^4$ |
| CHG + | 0.05 | |
| Sensiva | 1.0 | |
| BZK + | 0.12 | 0 |
| CHG + | 0.05 | |
| Sensiva | 2.0 | |
| BZK + | 0.12 | 0 |
| CHG + | 0.05 | |
| Sensiva + | 1.0 | |
| PXE | 1.0 | |
| BZK + | 0.12 | $8.0 \times 10^3$ |
| PHMB + | 0.3 | |
| Sensiva | 1.0 | |
| BZK + | 0.12 | 0 |
| PHMB + | 0.3 | |
| Sensiva + | 1.0 | |
| PXE | 1.0 | |

The above data demonstrates that the addition of the phenol derivative, phenoxyethanol, enhanced the antimicrobial activity of several combinations of Sensiva and other antimicrobials.

Example 7

Sustained Activity of Antimicrobial Preparations

Natural leather was cut into 2×2 cm pieces, washed, and sterilized. For each test group 4 pieces were used. Equal amounts (0.25 ml) of various test formulations were applied uniformly on the surface of each piece, and then allowed to dry for 3 hours. Then 10 microliters of a *Staphylococcus aureus* culture ($10^7$ CFU/ml) was spread uniformly on the surface of the treated leather patches. After 1 minute, the inoculated side of the leather was rinsed with 10 ml of drug-inactivating medium (LTSB), of which a 0.5 ml aliquot was plated on the surface of a D/E (drug-inactivating) plate. Plates prepared in this manner were incubated for 24 hours at 37° C. and bacterial colonies were counted. The results, which demonstrate sustained antimicrobial activity of the Sensiva formulations, are shown in Table 9.

TABLE 9

| Group | Staphylococcus aureus CFU/patch |
|---|---|
| 0.12% BZK + 0.5% PXE + 0.05% CHG + 1.0% Sensiva | 30 |
| 0.12% BZK + 0.5% PXE + 0.3% PHMB + 1.0% Sensiva | 20 |
| Prevacare | $1.3 \times 10^4$ |
| Gel Base (control) | $1.1 \times 10^4$ |
| Control | $1.2 \times 10^5$ |

Example 8

Aqueous Sensiva Formulation

For the experiments to be described below, the following aqueous base was used:

| | |
|---|---|
| hydroxy methyl propyl cellulose (K100M) | 0.5 percent |
| Kytamer PC (Chitisan) | 0.15 percent |
| U-care JR-400 | 0.1 percent |
| Incroquat Behenyl TMS | 1.0 percent |
| Crodamol NM | 1.6 percent |
| Acetulan | 2.0 percent |
| Cremerol HMG | 1.0 percent |
| stearyl alcohol | 2.0 percent |
| allantoin | 0.25 percent |
| Germall Plus | 0.3 percent |
| dimethicone | 1.0 percent (volume/volume) | and then water was added to bring to volume up to 100 percent. Various antimicrobials were added to this aqueous base, and then tested according to the protocol set forth in Example 1. The results are shown in Table 10.

TABLE 10

| Group | Staphylococcus aureus (CFU/tube) |
|---|---|
| aqueous base (control) | $5.0 \times 10^8$ |
| 0.12% BZK | $2.0 \times 10^8$ |
| 1.0% PXE | $1.0 \times 10^8$ |
| 0.5% PXE | $3.4 \times 10^8$ |
| 1.0% Sensiva | $5.0 \times 10^8$ |
| 0.05% CHG | $2.5 \times 10^8$ |
| 0.3% PHMB | $1.0 \times 10^7$ |
| 1% PXE + 1% Sensiva | $1.0 \times 10^8$ |
| 0.05% CHG + 1% Sensiva | $5.0 \times 10^6$ |
| 0.05% CHG + 1% PXE | $1.0 \times 10^8$ |
| 0.12% BZK + 1% Sensiva | $2.5 \times 10^6$ |
| 0.12% BZK + 1% PXE | $1.2 \times 10^7$ |
| 0.12% BZK + 1% PXE + 1% Sensiva | $4.0 \times 10^4$ |
| 0.12% BZK + 0.5% PXE + 0.05% CHG | $2.0 \times 10^5$ |
| 0.12% BZK + 0.5% PXE + 0.05% CHG + 0.3% PHMB | $2.7 \times 10^4$ |
| 0.12% BZK + 0.5% PXE + 0.05% CHG + 1% Sensiva | 0 |
| 0.12% BZK + 0.5% PXE + 0.3% PHMB + 1% Sensiva | 0 |
| 0.12% BZK + 0.5% PXE + 0.05% CHG + 0.3% PHMB + 1% Sensiva | 0 |
| negative control (no base/no agent) | $8.0 \times 10^8$ |

The foregoing experiments indicate that the potentiation of the antimicrobial activity of agents by Sensiva occurs in aqueous solution, in addition to the results observed using alcoholic gels. A combination of BZK, biguanide (CHG or PHMB), PXE and Sensiva achieved complete kill of test bacteria within 15 seconds.

Example 9

Sustained Activity of Aqueous Formulations

Various combinations of antimicrobials were incorporated in an aqueous base, as set forth in Example 8, and then tested for sustained activity on leather patches using the protocol set forth in Example 7. The results, which demonstrate enhanced sustained activity in the presence of Sensiva, are shown in Table 11.

TABLE 11

| Group | Staphylococcus aureus (CFU/patch) |
|---|---|
| 0.12% BZK + 0.5% PXE + 0.05% CHG + 0.3% PHMB | $2.0 \times 10^4$ |
| 0.12% BZK + 0.5% PXE + 0.05% CHG + 0.3% PHMB + 1% Sensiva | 0 |
| Aqueous Base (control) | $5.0 \times 10^5$ |
| Negative Control (no agent/no base) | $5.4 \times 10^5$ |

Example 10

Alcohol Gels Containing Sensiva and Zinc Anti-Irritants

In individuals whose skin is sensitive to alcohol or antiseptics, the use of antimicrobial alcoholic gels can be irritating, and may cause dermatitis. It has been found that certain zinc salts, selected from the group of zinc gluconate, zinc oxide and zinc stearate, can provide an anti-irritant effect (see U.S. Pat. No. 5,965,610 by Modak et al., issued Oct. 12, 1999 and U.S. Pat. No. 5,985,918 by Modak et al., issued Nov. 16, 1999). In alcohol gel formulations containing Sensiva, zinc compounds were added in irritation-preventing quantities and their antimicrobial effectiveness was tested. The formulation was as follows:

| | |
|---|---|
| zinc gluconate | 2.0 percent |
| ethanol | 63.5 percent (volume/volume) |
| Kytamer PC (Chitisan) | 0.1 percent |
| U-care JR 400 (polyquaternium 10) | 0.08 percent |
| Germall Plus | 0.3 percent |
| Crodamol MM | 0.9 percent |
| Acetulan | 0.5 percent |
| Cremerol HMG | 1.0 percent |
| Incroquat | 1.5 percent |
| Polawax A-31 | 2.0 percent |
| hydroxy methyl propyl cellulose (K100M) | 0.4 percent |
| zinc stearate | 3.5 percent |
| allantoin | 0.2 percent |
| dimethicone | 0.5 percent (volume/volume) |
| propylene glycol | 1.5 percent (volume/volume) |
| glycerin | 1.0 percent (volume/volume) |
| Sensiva | 1.5 percent (volume/volume) |
| PXE | 1.0 percent |
| BZK | 0.12 percent |
| PHMB | 0.3 percent | and water was added to 100% (approx. 18 ml/100 ml formulation). The resulting formulation is referred to as a "cream".

To test for rapid antimicrobial activity, 0.8 ml of the above cream formulation was mixed with 0.1 ml of $10^9$/ml CFU of test organisms and 0.1 ml bovine adult serum. After 15 seconds, this mixture was diluted 1000-fold with LTSB drug-inactivating media and 0.5 ml of the resulting solution was subcultured on a TSA plate. The resulting plates were incubated for 24 hours at 37° C. and bacterial counts per tube were determined. To test for sustained antimicrobial activity, the method set forth in Example 7, using leather patches, was employed. The results of testing for rapid and sustained antimicrobial activities are shown in Table 12.

TABLE 12

| Formulation | Rapid Activity (CFU/tube) | Sustained Activity (CFU/patch) |
|---|---|---|
| Zn Gluconate 2% + Zn Stearate 3.5% + Sensiva 1.5% + PXE 1% + BZK 0.12% + PHMB 0.3% – containing cream* | 0 | 40 |
| Prevacare | 0 | $9.2 \times 10^3$ |
| Cream Without Antimicrobials ** | $2.8 \times 10^5$ | $8.6 \times 10^3$ |
| Control | $6.5 \times 10^8$ | $2.3 \times 10^5$ |

*as comprised in the formulation set forth above in this example section.
**the formulation set forth above, omitting Sensiva, PXE, BZK and PHMB Example 11

Antiseptic Alcohol Gel Formulation Containing Zinc Salts

The following gel formulation has only a small amount of zinc salts. It was tested for rapid antimicrobial activity against *Staphylococcus aureus*, *Pseudomonas aeruginosa*, and *Escherichia coli* using the protocol set forth in Example 10. The results, which indicate that the formulation has activity against gram positive (*Staphylococcus aureus*) as well as gram negative (*Pseudomonas aeruginosa* and *Escherichia coli*) are shown in Table 13.

| ethyl alcohol | 63.5 percent (volume/volume) |
|---|---|
| zinc gluconate | 0.8 percent |
| zinc oxide | 0.25 percent |
| hydroxy methyl propyl cellulose (K100M) | 0.4 percent |
| Glucam P20 | 1.0 percent (volume/volume) |
| Glucam P20 distearate | 1.5 percent (volume/volume) |
| U-care JR400 | 0.15 percent |
| silicone (DC 1403) | 1.5 percent (volume/volume) |
| Germall Plus | 0.25 percent |
| PHMB | 0.3 percent |
| PXE | 1.5 percent |
| BZK | 0.12 percent |
| Sensiva | 1.5 percent | with water added to 100 percent (approx. 27.2 ml/100 ml).

TABLE 13

| Formulation | S. aureus CFU/tube | P. aeruginosa CFU/tube | E. coli CFU/tube |
|---|---|---|---|
| Zn gluconate 0.8% + Zn oxide 0.2% + PHMB 0.3% + PXE 1.5% + BZK 0.12% + Sensiva 1.5% gel* | 0 | $1.0 \times 10^3$ | 0 |
| Prevacare | 0 | ND | ND |
| Alcohol Gel Without Antimicrobials** | $3.2 \times 10^5$ | $5.0 \times 10^7$ | $1.0 \times 10^7$ |
| Control | $8.0 \times 10^8$ | $5.0 \times 10^8$ | $6.5 \times 10^8$ |

*gel formulation set forth above in this example section.
**gel formulation set forth above, lacking PHMB, PXE, BZK and Sensiva.

Example 12

Foaming Antimicrobial Gel

The following alcoholic foam formulation was prepared and tested for rapid antimicrobial activity according to the method set forth in Example 10, using *Staphylococcus aureus* as the test organism. The results are shown in Table 14. If more foaming is desired, a surfactant, such as lauroyl ethylenediamine triacetic acid sodium salt (0.5-2.0%) may be added to the following formulation.

| zinc gluconate | 0.25 percent |
|---|---|
| zinc acetate | 0.25 percent |
| ethanol | 65.0 percent (volume/volume) |
| Polyquaternium 22 | 2.0 percent |
| Pluronic Gel (F-87) | 0.075 percent (volume/volume) |
| BZK | 0.12 percent |
| CHG | 0.05% |
| PXE | 1.0 percent |
| Sensiva | 1.0 percent (volume/volume) | with water added to 100 percent (approx. 30.25 ml/100 ml).

TABLE 14

| Formulation | S. aureus CFU/tube |
|---|---|
| BZK 0.12% + CHG 0.05% + PXE 1.0% + Sensiva 1.0% foam (supra) | 0 |
| Above Foam Without BZK, CHG, PXE or Sensiva | $2.0 \times 10^5$ |
| Control | $3.9 \times 10^8$ |

Example 13

Method of Preparing Hydroalcoholic Gel Compositions

The novel hydroalcoholic gel compositions of the present invention are made according to the following process:

water phase—one or more hydrogels are dissolved in water at ambient temperature, preferably the hydrogel is present in a concentration of between 0.05 and 0.5 percent and water is present in a concentration of between 15 and 70 percent;

alcohol phase—one or more emollient are dissolved in alcohol at ambient temperature, preferably the alcohol is present in a concentration between 30 and 95 percent and the emollient is present in a concentration of between 0.2 and 3.0 percent;

thereafter, the water phase and the alcohol phase are mixed together at ambient temperature;

once combined, additional compositions can be added, including silicone polymers, thickeners, emulsifiers, emollient solvent and antimicrobial agents.

Hereafter, all percentages should be considered weight/weight percentages, unless specified otherwise.

Each of the following five hydroalcoholic gel compositions were made according to the following method:

0.3% K100M hydrogel was dissolved in water at ambient temperature;

one or more emulsifiers were dissolved in ethanol at ambient temperature;

the dissolved hydrogels and dissolved emulsifiers were mixed together at ambient temperature;

thereafter, the additional ingredients of 2.0 percent glycerin, 0.2 percent silicone glycol (BASF 1066-DCG Polyol) and antimicrobial agents were added; and the total weight of the gel was adjusted to 100 percent without affecting the relative amount of antimicrobial agent.

The amounts of emulsifiers and antimicrobial agents of Samples 1-5 are presented below in Table 15.

TABLE 15

| Sample | Emulsifiers | Antimicrobials |
|---|---|---|
| 1 | 1% Incroquat + 1% Polawax | 1% chlorhexidine |
| 2 | 2% Incroquat | 1% chlorhexidine |
| 3 | 1% Incroquat | 1% chlorhexidine |
| 4 | 2% Incroquat | 0.12% BZK + 0.5% Phenoxyethanol |
| 5 | 2% Incroquat | None |

Example 14

Antimicrobial Efficacy Varies Using Bases of Different Composition

Two commercially available compositions were including in this study: Avagard (Sample 6) and Prevacare (Sample 7). The amounts of thickeners, emulsifiers and antimicrobial agents are set out below in Table 16.

TABLE 16

| Sample | Thickeners/Emulsifier | Antimicrobials |
|---|---|---|
| 6 | Beheneth-10 + Behenyl Alcohol + Cetyl Palmitate + Diisopropyl dimer dilinoleate | 1% chlorhexidine |
| 7 | Stearyl alcohol + coco PG dimonium chloride phosphate + PEG 8000 (carbomer) | 0.12% BZK + 0.5% Phenoxyethanol |

Samples 1-7 were then evaluated to compare the efficacy of the antimicrobial agents incorporated into different base compositions according to the following method:
  3×3 cm pieces of pigskin were mounted on plastic plate holders of 5 cm diameter with epoxy to expose the skin surface;
  two pieces of skin were used for each sample;
  0.3 ml of each Sample 1-7 was placed on one of the two pieces;
  the two pieces were rubbed adjacent each other for 30 seconds and dried for 15 minutes at room temperature in an uncovered petridish;
  one of the two pieces was inoculated with 50 µl of a test culture of $10^7$ colony-forming units (cfu/ml);
  the inoculated piece was rubbed on the other piece for 15 seconds;
  after 30 seconds, 0.2 ml of LTSB was applied on one of the two pieces;
  the two pieces were rubbed together for 15 seconds and each piece was rinsed with 4.9 ml of LTSB;
  after 1:10 dilution with LTSB, 0.5 ml aliquot was plated on TSA plates;
  plates were inoculated for 24 hours at 37° C.; and
  thereafter bacterial cfu per plate were counted.

The results after 15 seconds as part application of the sample are shown below in Table 17.

TABLE 17

| Sample | Antimicrobials | Activity (cfu/plate) |
|---|---|---|
| 5 | None | 1376 |
| 1 | 1% chlorhexidine | 337 |
| 2 | 1% chlorhexidine | 320 |
| 3 | 1% chlorhexidine | 240 |
| 6 | 1% chlorhexidine | 1428 |
| 4 | BZK + Phenoxyethanol | 181 |
| 7 | BZK + Phenoxyethanol | 1760 |

From these results, it is evident that the antimicrobial effectiveness varies by changing the composition of the base of the present invention. Further, it can be seen that the gel compositions of the present invention (Samples 1-5) provide greater antimicrobial efficacy with equivalent amounts of antimicrobial agents than the in prior art compositions (Samples 6-7). Without being bound to any particular theory, it is predicted that the thickeners and emulsifiers used in the prior art compositions (Samples 6 and 7) interfere with the antimicrobial agent. It is also notable that Sample 5 of the present invention which did not contain any additional antimicrobial agent yielded better antimicrobial activity than both of the commercially available formulations of Avagard (Sample 6) and Prevacare (Sample 7).

Example 15

Broad Spectrum of Antimicrobial Activity

In order to study the spectrum of antimicrobial activity, another hydroalcoholic gel composition (Sample 8) was made according to the following method:
  the hydrogel polyquarternium-10 (U-care JR 30) was dissolved in water at ambient temperature;
  the emulsifiers Incroquot Behenyl TMS and Polawax A31 were dissolved in ethanol at ambient temperature;
  the dissolved hydrogel and dissolved emulsifers were mixed together at ambient temperature;
  thereafter, the emollients Kytamer L and octoxyglycerin; the antimicrobials agents, chlorhexidrine gluconate, benzalkonium chloride, and phenoxyethanol; and silicone glycol (BASF 1066-DCG Polyol) were added.

The amounts of the ingredients specified above for Sample 8 are set forth below in Table 18.

TABLE 18

| Ingredients | percentage (w/w) |
|---|---|
| Water* | 30.6 |
| polyquaternium-10 (U-care JR30) | 0.2 |
| Kytamer L | .1 |
| Ethanol | 65 |
| Incroquat Behenyl TMS | 0.8 |
| Polawax A-31 | 0.4 |
| octoxyglycerin | 2.0 |
| chlorhexidine gluconate | 0.05 |
| benzalkonium chloride (BZK) | 0.12 |
| phenoxyethanol | 0.5 |
| silicone glycol (BASF 1066-DGC Polyol) | 0.2 |

*Water was added to bring the volume up to 100 percent.

Antimicrobial activity was evaluated using the following method comparing Sample 8, Prevacare, Avagard and a control of phosphate-buffered saline:
  sterile pig skin was cut into 3×3 cm sections that were mounted on plastic plate holders of 5 cm diameter with epoxy so that one side was exposed;
  two pieces of skin were used for each sample;

30 μl aliquot of the test organism containing $10^7$ colony-forming units (cfu/ml) was inoculated on one of the pieces;

the inoculated piece was rubbed on the other piece for 15 seconds;

after 5 minutes, 0.3 ml of the test product was applied on one of the two pieces and rubbed onto the other piece for 15 seconds;

each skin section was rinsed with 4.9 ml of LTSB to recover viable organisms;

the recovered medium is further diluted 1:10 with LTSB and 0.5 ml aliquot was subcultured on TSA plate;

the plates were incubated for 24 hours at 37° C.?;

thereafter bacterial cfu per plate were counted.

The results after 15 seconds post-application of each test product are shown below in Table 19.

TABLE 19

| | CFU per sample treated with | | | |
|---|---|---|---|---|
| Test Organism | Sample 8 | Prevacare | Avagard | Control (PBS) |
| S. epidermidis | 0 | 54 | 70 | $9.3 \times 10^4$ |
| S. aureus | 0 | 58 | 48 | $2.3 \times 10^5$ |
| MRSA | 0 | ND | ND | $9.8 \times 10^3$ |
| VREF | 0 | ND | ND | $9.4 \times 10^3$ |
| E. aerogenes | 0 | ND | ND | $9.5 \times 10^3$ |
| A. baumanni | 0 | ND | ND | $9.3 \times 10^3$ |
| K. pneumoniae | 0 | ND | ND | $9.3 \times 10^3$ |
| E. coli | 0 | 150 | 5 | $1.9 \times 10^4$ |
| P. aeruginosa | 0 | 0 | 0 | $2.4 \times 10^4$ |

ND = Not Done

The data shown above indicates that the application of Sample 8 resulted in more effective antibacterial activity than what would have been expected based on the results of the prior art samples of Prevacare and Avagard when tested against S. epidermidis, S. aureus and E. coli. Also, the data in Table 19 demonstrates an effective antibacterial activity of Sample 8 across a broad spectrum of test organisms.

Example 16

Sustained Efficacy Against S. aureus

Another hydroalcoholic gel composition made in accordance with this invention (Sample 9) was formulated according to the method set forth in Example 15 above, except that 2.0 percent glycerin was substituted for 2.0 percent octoxyglycerin.

In order to study the sustained efficacy, Samples 8 and 9 were compared with samples of Prevacare, Avagard and a control of 60 percent ethyl alcohol in a gel base with no preservatives, according to the following method:

sterile pig skin was cut into 3×3 cm sections that were mounted on plastic plate holders of 5 cm diameter with epoxy so that one side was exposed;

two pieces of skin were used for each sample;

0.3 ml aliquot of the test formulation was inoculated on one of the pieces;

the inoculated piece was rubbed on the other piece for 30 seconds;

the inoculated piece was left at room temperature for the time period specified below in Table 20;

after the specified time, 30 μl of *Staphylococcus aureus* containing $10^7$ cfu/ml was applied to one of the two pieces and rubbed on the other piece for 15 seconds;

the samples were subcultured after 30 seconds following the same procedure set forth in Example 15.

The results after 15 minutes, 2 hours, and 3 hours post-application time of Sample 8, Sample 9, Prevacare, Avagard and the control are shown below in Table 20.

TABLE 20

| | CFU/sample | | |
|---|---|---|---|
| Sample | 15 min | 2 hours | 3 hours |
| 8 | 31 | 55 | 190 |
| 9 | 200 | ND | ND |
| Prevacare | $1.5 \times 10^5$ | $9.5 \times 10^3$ | $3.1 \times 10^4$ |
| Avagard | $2.6 \times 10^6$ | ND | ND |
| Control | $2.5 \times 10^5$ | $9.2 \times 10^3$ | $4.0 \times 10^4$ |

ND = Not Done

The data illustrated in Table 20 above indicates the sustained efficacy of the antimicrobial activity of Samples 8 and 9 which is significantly greater than expected when compared with the samples of Prevacare and Avagard when tested against S. aureus.

Example 17

Rapid and Sustained Antimicrobial Efficacy Demonstrated In Vivo

In vivo tests were performed on four volunteers to assess the rapid efficacy of hydroalcoholic gel composition (Sample 8) compared with Prevacare, Avagard and a control of phosphate-buffered saline, according to the method specified below. The order in which the products were tested were varied each of the three times the experiments were repeated. Each volunteer disinfected their hands with 70% ethanol alcohol and dried them thoroughly before beginning the following procedure:

both hands of each volunteer were inoculated with 1 ml containing $10^6$ cfu/ml of *Staphylococcus epidermidis* isolated from each volunteer's flora;

after 5 minutes, 2 ml of the test product were applied to both hands of each volunteer;

after 15 seconds the three middle fingers of each hand were rinsed with drug-inactivating media to recover any viable organisms according to the method set forth in Example 15;

a diluted aliquot of the rinsed solution was plated on a drug-neutralizing (D/E) agar accordingly to the method set forth in Example 15 to count the number of surviving colony forming units.

The results 5 minutes after contaminations with S. epidermidis and 15 seconds post-application of the first product are shown in Table 21 below:

TABLE 21

| Sample | cfu/ml (15 sec, post-application of sample) |
|---|---|
| 8 | 2 |
| Prevacare | 66 |
| Avagard | 13.3 |
| Control | 9600 |

In vivo tests were performed on the same four volunteers to assess the sustained efficacy of hydroalcoholic gel composition (Sample 8) compared with commercially available formulations of Prevacare, Avagard, Purell (62% ethyl alcohol), Hibiclens (4% chlorhexidine gluconate) and Betadine (10% poviodine iodine with 1% available iodine), and a control (60% ethyl alcohol in a gel base with no preservatives) according to the following method:

- each volunteer disinfected their hands with 70% ethanol alcohol and dried them thoroughly (the order in which the products were tested was varied each of the three times the experiments were repeated);
- both hands were inoculated with 2 ml containing the test product;
- fifteen minutes after inoculation of the test product, the middle three fingers of one hand were inoculated with 30 μl of *Staphylococcus epidermidis* culture containing $10^7$ cfu/ml isolated from each volunteer's own flora;
- after 30 seconds the fingers were rinsed with a drug-inactivating recovery medium according to the method set forth in Example 15;
- a diluted aliquot of the rinsed solution was subcultured on drug-neutralizing agar plates to count the number of surviving colony forming units.

The results 15 minutes after application of the test product and 30 seconds after exposure to *S. epidermidis* are shown below in Table 22:

TABLE 22

| Sample | cfu/ml (30 seconds post exposure) |
|---|---|
| 8 | 40 |
| Prevacare | $2.1 \times 10^4$ |
| Avagard | $3.1 \times 10^3$ |
| Purell | $2.9 \times 10^4$ |
| Hibiclens | $3.0 \times 10^4$ |
| Betadine | $8.8 \times 10^3$ |
| Control | $1.1 \times 10^4$ |

The data of Tables 21 and 22 demonstrate the rapid and sustained antimicrobial efficacy of the hydroalcoholic gel composition (Sample 8) made according to the present invention in vivo over commercially available products.

Example 18

Even Better Results at Lower Viscosities Against *S. aureus*

Four additional samples were prepared in accordance with this invention and according to the method of Example 13 having the formulations set forth in Table 23 (Sample 10), Table 24 (Sample 11), Table 25 (Sample 12), and Table 26 (Sample 13) below. The control base was prepared according to formulation set forth in Table 27 (Control). These Samples 10-13 have a lower viscosity than the prior Samples 1-5 and 8-9. The range of viscosity of Samples 1-5 and 8-9 is about 1200 to 1500 cps, with Sample 8 having a viscosity of about 1500 at 20 C. The range of viscosity of Samples 10-13 is 50-200 at 20 C and about 30-50 at 40 C, with Sample 10 being about 55 at 20 C. Viscosity was measured using Brookfield model LVT Spindle No. 2 60 RPM.

TABLE 23

(Sample 10)

| Ingredients | Percentage (w/w) |
|---|---|
| Water | 31.73 |
| Polyquaternium-10 (U-care JR30) | 0.2 |

TABLE 23-continued (Sample 10)

| Ingredients | Percentage (w/w) |
|---|---|
| Ethanol | 65 |
| Incroquat behenyl TMS | 0.4 |
| Octoxy Glycerin | 2 |
| Chlorhexidine gluconate | 0.05 |
| Benzalkoniumchloride | 0.12 |
| Phenoxyethanol | 0.5 |

TABLE 24

(Sample 11)

| Ingredients | Percentage (w/w) |
|---|---|
| Water | 31.73 |
| Polyquaternium-10 (U-care JR30) | 0.2 |
| Ethanol | 65 |
| Incroquat behenyl TMS | 0.4 |
| Glycerin | 2 |
| Chlorhexidine gluconate | 0.05 |
| Benzalkoniumchloride | 0.12 |
| Phenoxyethanol | 0.5 |

TABLE 25

(Sample 12)

| Ingredients | Percentage (w/w) |
|---|---|
| Water | 33.73 |
| Polyquaternium-10 (U-care JR30) | 0.2 |
| Ethanol | 65 |
| Isopropanol | 5 |
| Incroquat behenyl TMS | 0.4 |
| Octoxy Glycerin | 2 |
| Chlorhexidine gluconate | 0.05 |
| Benzalkoniumchloride | 0.12 |
| Phenoxyethanol | 0.5 |

TABLE 26

(Sample 13)

| Ingredients | Percentage (w/w) |
|---|---|
| Water | 26.73 |
| Polyquaternium-10 (U-care JR30) | 0.2 |
| Ethanol | 65 |
| Isopropanol | 5 |
| Incroquat behenyl TMS | 0.4 |
| Glycerin | 2 |
| Chlorhexidine gluconate | 0.05 |
| Benzalkoniumchloride | 0.12 |
| Phenoxyethanol | 0.5 |

TABLE 27

(Control)

| Ingredients | Percentage (w/w) |
|---|---|
| Water | 31.73 |
| Polyquaternium-10 (U-care JR30) | 0.2 |
| Ethanol | 65 |
| Incroquat behenyl TMS | 0.4 |
| Octoxy Glycerin | 2 |

The sustained efficacy of these hydroalcoholic gel compositions having lower viscosities (Samples 10, 11, 12, and 13) were compared with Sample 8, Prevacare, Avagard and a control of 60 percent ethyl alcohol in a gel base with no preservatives, according to the following method:

sterile pig skin was cut into 3×3 cm sections that were mounted on plastic plate holders of 5 cm diameter with epoxy so that one side was exposed;
two pieces of skin were used for each sample;
0.3 ml aliquot of the test formulation was inoculated on one of the pieces;
the inoculated piece was rubbed on the other piece for 30 seconds;
the inoculated piece was left at room temperature for 15 minutes;
after 15 minutes, 30 μl of staphylococcus aureus containing $10^7$ cfu/ml was applied to one of the two pieces and rubbed on the other piece for 15 seconds;
the samples were subcultured after 30 seconds following the same procedure set forth in Example 15.

The results after 15 minutes post-application time of Samples 8, 10, 11, 12 and 13, Purell, Avagard and the control are shown below in Table 20.

TABLE 28

| Sample | 15 min. (cfu/sample) |
|---|---|
| 8 | 40 |
| 10 | 0 |
| 11 | 0 |
| 12 | 0 |
| 13 | 0 |
| Purell | $1.1 \times 10^5$ |
| Avagard | $3.9 \times 10^4$ |
| Control | $2.0 \times 10^5$ |

The data of Table 28 indicates the efficacy of the antimicrobial activity of Samples 8, 10, 11, 12, and 13 in comparison with the prior art products of Purell and Avagard. Further, Samples 10-13, having lower viscosities that Sample 8 demonstrated superior results when tested against S. aureus.

Example 19

Reduction of Hand Flora

A surgical scrub was prepared in accordance with this invention and according to the method of Example 13 having the formulation set forth in Table 29 below.

TABLE 29

(Sample 14)

| Ingredients | percentage (w/w) |
|---|---|
| Water | 26.8 |
| U care JR30 | 0.3 |
| Ethanol | 70 |
| Octoxy Glycerin | 2 |
| Silicone Glycol (BASF 1066-DCG Polyol) | 0.2 |
| Chlorhexidine gluconate | 0.05 |
| Benzalkoniumchloride | 0.12 |
| Phenoxyethanol | 0.5 |

In order to assess the efficacy of this formation of inhibiting hand flora, Sample 14 was compared with Betadine scrub (10% PVI in non-alcoholic bases) and Avagard, according to the following method:

each volunteer washed hands with plain soap and water;
each volunteer applied each of the test products according to the manufacturer's instructions;
For Betadine—Hands were wet with water; 5 cc of Betadine surgical scrub was poured on the palm of the hand and spread over both the hands; the scrub was rubbed thoroughly over all the areas of the hand for about 5 min; fingernails were thoroughly cleaned; hands were rinsed thoroughly under running water; wash was completed by scrubbing with another 5 cc of the Betadine scrub in the same manner;
For Avagard—2 ml of Avagard was dispensed into the palm of one hand; the fingertips of the opposite hand was dipped into the Avagard; the remaining Avagard was spread over the hand just above the wrist; 2 ml was dispensed for the other hand and applied in the same manner; another 2 ml of Avagard was reapplied on both hands up to the wrist; and
For Sample 14—the method used was same as the method used for Avagard;
thereafter, each hand was placed in a sterile latex glove;
one minute after use of the product, 50 ml of sterile phosphate buffered saline (PBS) was added to each glove and the hands were massaged in a uniform manner for one minute;
the resulting "glove juice" extract was then diluted using a drug inactivating media and subcultured on agar plates to determine colony counts.

The percent reduction of hand flora one minute after treatment are shown in Table 30 below.

TABLE 30

| Sample | Base Line Counts | 1 min. post counts | percent reduction |
|---|---|---|---|
| Sample 14 | $1.4 \times 10^5$ | $1.3 \times 10^4$ | 90.7 |
| Betadine | $2.6 \times 10^5$ | $7.4 \times 10^4$ | 71.6 |
| Avagard | $1.4 \times 10^5$ | $1.5 \times 10^5$ | 0 |

Various publications are cited herein, the contents of which are hereby incorporated herein in their entireties by reference.

We claim:

1. A hydroalcoholic gel composition comprising:
   between 30 and 95 percent (weight/weight) alcohol,
   water,
   between 0.05 and 0.5 percent (weight/weight) hydrogel,
   between 0.2 and 3.0 percent (weight/weight) emollient,
   between 1.0 and 5.0 percent (weight/weight) octoxyglycerin, and
   between 0.01 and 0.3 percent (weight/weight) of a quaternary ammonium compound, wherein the octoxyglycerin and quaternary ammonium compound are present in amounts which exhibit synergistic antimicrobial activity, and further wherein said composition has a viscosity below 2000 centipoises.

2. The composition of claim 1 which further comprises between 0.05 and 0.5 percent emulsifier.

3. The composition of claim 1 which further comprises between 0.1 and 1.0 percent silicone polymer.

4. The composition of claim 1 which further comprises between 0.5 and 5.0 percent emollient solvent.

5. The composition of claim 1 which further comprises between 0.1 and 1.0 percent thickening agent.

6. The composition of claim 1 wherein the hydrogel is cationic hydroxyethyl cellulose.

7. The composition of claim 1 wherein the emollient is PPG-20 methyl glucose ether.

8. The composition of claim 2 wherein the emulsifier is a composition comprising behentrimonium methosulfate, cetyl alcohol, and butylene glycol.

9. The composition of claim 3 wherein the silicone polymer is dimethiconol fluid in dimethicone.

10. The composition of claim 5 wherein the thickening agent is behenyl alcohol.

11. The composition of claim 1 wherein benzalkonium chloride is the quaternary ammonium compound.

12. The composition of claim 1 wherein the alcohol is an aliphatic alcohol.

13. The composition of claim 12 wherein the aliphatic alcohol is ethanol.

14. The composition of claim 12 wherein the aliphatic alcohol is ethanol at a concentration of between 60 and 95 percent.

15. The composition of claim 1 wherein the emollient is PPG-3-myristyl ether.

* * * * *